(12) United States Patent
Hallinan et al.

(10) Patent No.: US 9,090,554 B2
(45) Date of Patent: Jul. 28, 2015

(54) PROCESS FOR THE MANUFACTURE OF ACETIC ACID

(71) Applicant: LyondellBasell Acetyls, LLC, Houston, TX (US)

(72) Inventors: Noel C. Hallinan, Loveland, OH (US); John D. Hearn, Beach City, TX (US); Michael E. Fitzpatrick, League City, TX (US); Miraj S. Patel, Sugar Land, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 236 days.

(21) Appl. No.: 13/713,930

(22) Filed: Dec. 13, 2012

(65) Prior Publication Data
US 2013/0296616 A1    Nov. 7, 2013

Related U.S. Application Data

(60) Provisional application No. 61/578,709, filed on Dec. 21, 2011.

(51) Int. Cl.
| C07C 51/42 | (2006.01) |
| C07C 51/44 | (2006.01) |
| C07C 51/12 | (2006.01) |
| C07C 51/48 | (2006.01) |

(52) U.S. Cl.
CPC ............... C07C 51/44 (2013.01); C07C 51/12 (2013.01); C07C 51/48 (2013.01)

(58) Field of Classification Search
CPC .......... C07C 51/12; C07C 51/44; C07C 51/48
See application file for complete search history.

(56) References Cited

U.S. PATENT DOCUMENTS

| 4,102,922 | A | | 7/1978 | Price |
| 4,908,477 | A | * | 3/1990 | Hartmann et al. ............ 560/248 |
| 5,001,259 | A | | 3/1991 | Smith et al. |
| 5,026,908 | A | | 6/1991 | Smith et al. |
| 5,144,068 | A | | 9/1992 | Smith et al. |
| 5,371,286 | A | | 12/1994 | Blay et al. |
| 5,599,976 | A | | 2/1997 | Scates et al. |
| 5,625,095 | A | | 4/1997 | Miura et al. |
| 5,723,660 | A | | 3/1998 | Morimoto et al. |
| 5,783,731 | A | | 7/1998 | Fisher et al. |
| 5,817,869 | A | | 10/1998 | Hinnenkamp et al. |
| 5,932,764 | A | | 8/1999 | Morris et al. |
| 6,143,930 | A | | 11/2000 | Singh et al. |
| 6,339,171 | B1 | | 1/2002 | Singh et al. |
| 6,552,221 | B1 | * | 4/2003 | Hallinan et al. .............. 562/519 |
| 7,208,624 | B2 | | 4/2007 | Scates et al. |
| 7,619,113 | B2 | | 11/2009 | Powell |
| 7,790,919 | B2 | | 9/2010 | Hallinan et al. |
| 7,790,920 | B2 | | 9/2010 | Brtko et al. |
| 7,812,191 | B2 | | 10/2010 | Hallinan et al. |
| 7,838,701 | B2 | | 11/2010 | Trueba et al. |
| 7,855,306 | B2 | | 12/2010 | Zinobile et al. |
| 2010/0228051 | A1 | | 9/2010 | Key et al. |

FOREIGN PATENT DOCUMENTS

| EP | 487284 A2 | 5/1992 |
| EP | 506240 A2 | 9/1992 |

OTHER PUBLICATIONS

PCT/US2012/069735 International Search Report and Written Opinion mailed Apr. 22, 2013.

* cited by examiner

*Primary Examiner* — Paul A Zucker

(57) ABSTRACT

The phase separation in the decanter of a process for producing acetic acid by carbonylating methanol in the presence of a catalyst under low water-high acid conditions is improved by forming a liquid mixture (D) which has a water content of at most 20% by weight, based on the weight of the liquid mixture, and a weight ratio of acetic acid to water of at least 1:1, and partitioning the liquid mixture by providing for an alkane(s) content of D of from 0.1 to 15% by weight, based on the weight of D, to obtain a light, aqueous phase and a heavy, organic phase.

18 Claims, 6 Drawing Sheets

PROCESS FOR THE MANUFACTURE OF ACETIC ACID

CROSS REFERENCE TO RELATED APPLICATIONS

This application claims benefit of priority of U.S. Provisional Application No. 61/578,709 filed on Dec. 21, 2011, which is incorporated herein by reference in its entirety.

TECHNICAL FIELD

The disclosure relates to an improved process for producing acetic acid by carbonylating methanol in the presence of a catalyst. More particularly, the disclosure relates to a process which improves the phase separation of a condensed light ends overhead stream in cases where the overhead stream comprises high amounts of acetic acid and low amounts of water. Further, the disclosure relates to a method for expediting phase separation of a mixture comprising acetic acid, methyl iodide, and minor amounts of water.

BACKGROUND OF THE INVENTION

The manufacture of acetic acid by carbonylating methanol in the presence of a catalyst is of major industrial importance as acetic acid is employed in a wide variety of applications. The reaction for producing acetic acid can be represented by the following equation:

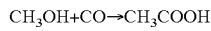

However, the underlying chemistry is intricate and involves multiple interrelated reactions, by-products, and equilibria. To be practicable, a manufacturing process, therefore, has to balance those reactions, the associated by-products, and the purification of the product.

Prior to 1970, acetic acid was produced using a cobalt catalyst. A rhodium carbonyl iodide catalyst was developed in 1970 by Monsanto. The rhodium catalyst is considerably more active than the cobalt catalyst, which allows lower reaction pressure and temperature. Most importantly, the rhodium catalyst gives high selectivity to acetic acid.

One of the problems associated with the original Monsanto process is that a large amount of water (about 14% by weight of the reaction mixture) is needed to produce hydrogen in the reactor via the water-gas shift reaction

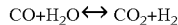

Water and hydrogen are necessary to react with precipitated Rh(III) and inactive [Rh$_4$(CO)$_2$] to regenerate the active Rh(I) catalyst. However, a large amount of water increases the formation of hydrogen iodide which, in turn, increases the formation of undesired by-products, such as long chain alkyl iodides, which are hard to separate from the acetic acid product. Further, removing a large amount of water from the acetic acid product renders the process more costly.

In the late 1970s, Celanese modified the carbonylation process by introducing lithium iodide to the reaction mixture. Lithium iodide increases the catalyst stability by minimizing side reactions which produce inactive Rh(III) species. Consequently, the amount of water which is necessary to stabilize the catalyst can be reduced. Additionally, lithium iodide has been found to decrease the vaporization tendency of water. See, e.g., European Publication 506 240. The process, thus, has advantages with regard to the separation of water and acetic acid.

Additionally, it has been discovered that catalyst stability and the productivity of the carbonylation reactor can be maintained at surprisingly high levels, even at very low water concentrations, i.e. 4%-wt. or less, in the reaction medium (despite the general industrial practice of maintaining approximately 14 wt. % or 15 wt. % water) by maintaining in the reaction medium, along with a catalytically effective amount of rhodium, at least a finite concentration of water, methyl acetate and methyl iodide, a specified concentration of iodide ions over and above the iodide content that is present as methyl iodide or other organic iodide. By using relatively high concentrations of the methyl acetate and iodide salt, a surprising degree of catalyst stability and reactor productivity has been achieved even when the water content of the liquid reaction medium is as low as about 0.1 wt. %. See, e.g., U.S. Pat. No. 5,001,259, U.S. Pat. No. 5,026,908 and U.S. Pat. No. 5,144,068. However, although the low water carbonylation process for the production of acetic acid reduces such by-products as carbon dioxide, hydrogen, and propionic acid, the amount of other impurities, present generally in trace amounts, is increased, and the quality of acetic acid sometimes suffers when attempts are made to increase the production rate by improving catalysts, or modifying reaction conditions.

Typically, acetic acid is produced in a plant which can be conveniently divided into three functional areas, i.e., the reaction, the light ends recovery, and the purification. In general, the reaction area comprises a reactor or reaction zone and a flash tank or flash zone. The light ends recovery area comprises a light ends distillation column or fractioning zone (also referred to in the art as "splitter" or "splitter column") and a phase separation vessel, e.g., a decanter. The light ends distillation column may also be part of the purification area, which in turn further comprises a drying column and optionally a heavy ends distillation column. See, e.g., U.S. Pat. No. 6,552,221.

The light ends recovery area inter alia serves to separate undesired by-products such as alkanes, carbonyl impurities, and alkyl iodide impurities. The overhead stream which is recovered from the light ends distillation column is condensed and phase separated in the decanter to obtain a light, aqueous phase comprising primarily acetic acid and water, and a heavy, organic phase comprising primarily methyl iodide, methyl acetate, and alkane impurities. The aqueous phase which is obtained in this manner can be treated to remove acetaldehyde and other carbonyl impurities before being recycled, e.g., to the light ends distillation column. See, e.g., U.S. Pat. No. 5,599,970, U.S. Pat. No. 5,625,095, U.S. Pat. No. 5,732,660, U.S. Pat. No. 5,783,731, U.S. Pat. No. 6,143,930, European Publication No. 0 487 284. The organic phase can be further purified to remove, e.g., the alkane impurities, and at least part of the purified methyl iodide is returned to the process. See, e.g., U.S. Pat. No. 4,102,922, U.S. Pat. No. 5,371,286, U.S. Pat. No. 5,723,660, and U.S. Pat. No. 7,812,191.

The proper operation of the decanter is a critical part of the overall performance of the acetic acid process. The phase separation time must be shorter than the residence time of the mixture to be phase separated in the decanter in order to ensure sufficient recycle of the methyl iodide promoter to the reaction zone which, in turn, ensures that the reaction rate in the reaction zone is maintained. If the phase separation in the decanter is incomplete, the methyl iodide phase which is recovered from the decanter is diluted. Recycling of the diluted methyl iodide causes destabilization of the reactor conditions manifested by, e.g., (1) upset of the water balance in the reactor; (2) increased energy consumption; (3) decreased reaction rate; and/or, (4) increased catalyst consumption. Additionally, dilution of the methyl iodide phase alters its density which interferes with the operation of downstream pumps and other in-line equipment.

However, as the water concentration in the reaction mixture is lowered (also referred to as "low water-high acid" or "low-water" conditions) and the methyl acetate concentration increases, the vapor load of the light ends distillation column increases which, in turn, causes a high carry-over of acetic acid into the decanter. The solubility of acetic acid in both the methyl iodide and aqueous phases causes the phase separation to deteriorate, eventually resulting in a single liquid phase in the decanter. When this condition occurs, the aqueous stream which is returned from the decanter to the light ends column includes a high amount of methyl iodide as well as impurities. The presence of this additional methyl iodide and impurities further interferes with the ability of the light ends column to cleanly separate light ends materials such as methyl acetate and impurities from the acetic acid product. Additionally, the failure of the condensed light ends overhead to separate into two phases in the decanter under low water-high acid process conditions interferes with the removal of undesired by-products from the process.

The problem of efficient and thorough phase separation in the decanter under low-water process conditions is known in the art and attempts have been made to ensure proper phase separation of the condensed overhead stream in the decanter. For example, U.S. Pat. No. 5,723,660 proposes to reduce the amount of methyl acetate, to significantly reduce the temperature to which the light ends overhead is cooled before it enters the decanter, or to batch-wise feed water into the light ends column to ensure that the methyl acetate concentration remains below 40 weight percent. However, these measures increase the process steps, thus increasing the costs. Also, feeding water into the light ends column to ensure that the methyl acetate concentration remains below 40 weight percent, is likely to significantly alter the water balance throughout the process each time water is added. An alternative approach to improving the phase separation in the decanter proposes the addition of effective amounts of dimethyl ether to the process to enhance the separation of the condensed overhead stream in the decanter, e.g., U.S. Pat. No. 7,208,624. However, dimethyl ether is difficult to handle, and the use of dimethyl ether gives rise to controllability problems, especially under steady state conditions, due to low boiling point of dimethyl ether (about 24° C.).

Accordingly, there continues to be a need to further improve the manufacture of acetic acid under low water-high acid conditions. In particular, there continues to be a need to improve and stabilize the phase separation in the decanter to ensure continuous and reliable removal of impurities.

SUMMARY OF THE DISCLOSURE

In general, the present disclosure provides a process for producing acetic acid. In one embodiment, the process for producing acetic acid comprises the steps of (1) reacting the starting materials in a reaction zone to form a reaction mixture comprising acetic acid; (2) separating the reaction mixture comprising acetic acid into a vapor stream that comprises acetic acid and a liquid stream; (3) separating the vapor stream into a product stream comprising an acetic acid and water mixture and an overhead stream; (4) condensing the overhead stream to form a liquid mixture; and, (5) partitioning the liquid mixture into a light, aqueous phase and a heavy organic phase.

In an additional or alternate embodiment, the process for producing acetic acid comprises the steps of: (1) reacting the starting materials in a reaction zone to form a reaction mixture comprising acetic acid; (2) separating the reaction mixture comprising acetic acid into a vapor stream that comprises acetic acid and a liquid stream; (3) separating the vapor stream into a product stream comprising an acetic acid and water mixture and an overhead stream; (4) condensing the overhead stream to form a liquid mixture; (5) partitioning the liquid mixture into a light, aqueous phase and a heavy organic phase; and, (6) separating the heavy organic phase into an overhead product and a bottom product.

In general embodiments, the starting materials include water, methyl acetate, methyl iodide, hydrogen, methanol, carbon monoxide. In additional embodiments, the reacting step takes place in the presence of a catalyst, a catalyst stabilizer and/or a catalyst promoter. In further embodiments, the reacting step takes place at a temperature of 120° C. to 250° C. and/or at a pressure ranging from about 200 psig to 2000 psig. In additional embodiments, the reacting step produces a reaction mixture comprising acetic acid, methyl acetate, methyl iodide, the catalyst, water and a vapor stream.

In a particular embodiment, the present disclosure relates to a process for producing acetic acid which comprises:
(a) carbonylating methanol in the presence of a catalyst in a reaction zone to obtain a reaction mixture (A) comprising acetic acid, methyl acetate, methyl iodide, the catalyst, and water;
(b) separating at least a part of the reaction mixture (A) in a flash zone to obtain a liquid stream ($B_L$) comprising the catalyst, and a vapor stream ($B_V$) comprising acetic acid, methyl acetate, methyl iodide, and water;
(c) separating the vapor stream ($B_V$) in a fractioning zone to obtain a product stream ($C_P$) comprising acetic acid and a minor amount of water, and an overhead stream ($C_O$) comprising acetic acid, methyl acetate, methyl iodide, and water;
(d) condensing the overhead stream ($C_O$) and forming a liquid mixture (D) which has a water content of at most 20% by weight, based on the weight of the liquid mixture, and a weight ratio of acetic acid to water of at least 1:1, and
(e) partitioning the liquid mixture (D) by providing for an alkane(s) content of D of from 0.1 to 15% by weight, based on the weight of D, to obtain a light, aqueous phase ($D_A$) comprising acetic acid and water, and a heavy, organic phase ($D_O$) comprising methyl iodide, methyl acetate, and the alkane(s).

In an additional embodiment, the present disclosure provides for a process in accordance with any of the foregoing embodiments, wherein the alkanes content of the liquid mixture (D) is provided by adding to $C_O$ one or more extraneous or innate alkanes, methyl iodide, acetic acid, or mixtures thereof, optionally in combination with innate water, provided that the resultant composition of D contains at most 20% by weight of water and contains acetic acid and water in a weight ratio of at least 1:1.

In a specific embodiment, the present disclosure provides for a process in accordance with any of the foregoing embodiments, wherein the extraneous or innate alkanes have at least 5 carbon atoms.

In a further embodiment, the present disclosure provides for a process in accordance with any of the foregoing embodiments, which further comprises separating the partitioned phases $D_A$ and $D_O$ to obtain an aqueous stream ($E_A$) and an organic stream ($E_O$), and providing the alkanes content of D by directly or indirectly recycling at least a part of the organic stream ($E_O$) to $C_O$.

In an additional and/or alternate embodiment, the present disclosure provides for a process in accordance with any of the foregoing embodiments, which comprises separating at least a part of the organic stream ($E_O$) to obtain an overhead product ($F_O$) comprising methyl iodide and at least a part of the alkanes, and a bottom product ($F_B$) comprising acetic acid, methyl acetate, water and optionally an additional part of the alkanes, and directly or indirectly recycling the overhead product ($F_O$) to the reaction zone, wherein the amount of the organic stream ($E_O$) and the separation thereof are adjusted such as to provide and maintain the alkanes content of $C_O$ at from 0.1 to 15% by weight, based on the weight of the condensed overhead stream ($C_O$).

In a specific embodiment, the present disclosure provides for a process in accordance with any of the foregoing embodiments, wherein the overhead stream ($C_O$) comprises at most 17% by weight of water.

In a particular embodiment, the present disclosure provides for a process in accordance with any of the foregoing embodiments, wherein the weight ratio of acetic acid to water in the overhead stream ($C_O$) is at least 1.5:1.

In one embodiment, the present disclosure provides for a process in accordance with any of the foregoing embodiments, wherein the overhead stream ($C_O$) comprises at least 15% by weight acetic acid.

In some embodiments, the present disclosure provides for a process in accordance with any of the foregoing embodiments, wherein the overhead stream ($C_O$) comprises at least 30% by weight methyl iodide.

In a further embodiment, the present disclosure provides for a process in accordance with any of the foregoing embodiments, wherein the alkanes content which is provided in the liquid mixture (D) is at least 0.5% by weight.

In a specific embodiment, the present disclosure provides for a process in accordance with any of the foregoing embodiments, wherein the alkanes content which is provided in the liquid mixture (D) is at most 13% by weight.

In a general embodiment, the present disclosure provides for a method for expediting phase separation of a mixture comprising acetic acid, methyl iodide, and minor amounts of water, which method comprises providing for an alkanes content of the mixture of from 0.1 to 15% by weight, based on the weight of the mixture.

In another embodiment, the present disclosure provides for a method in accordance with any of the foregoing embodiments, wherein the mixture comprises
  (i) from 35 to 90% by weight of methyl iodide,
  (ii) from 5 to 35% by weight of acetic acid,
  (iii) from 5 to 15% by weight of water, and
  (iv) up to 15% by weight of methyl acetate, the weight percentages in each case being based on the total weight of the components (i) to (iv), and wherein the weight ratio of acetic acid to water in the mixture is at least 1:1.

In a particular embodiment, the present disclosure provides for a method in accordance with any of the foregoing embodiments, wherein the alkanes content is provided by one or more alkanes each having at least 5 carbon atoms.

In a specific embodiment, the present disclosure provides for a method in accordance with any of the foregoing embodiments, wherein the alkanes content which is provided in the mixture is at least 0.5% by weight.

In a certain embodiment, the present disclosure provides for a method in accordance with any of the foregoing embodiments, wherein the alkanes content which is provided in the mixture is at most 12% by weight.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing.

DETAILED DESCRIPTION OF THE DISCLOSURE

Figure 1:
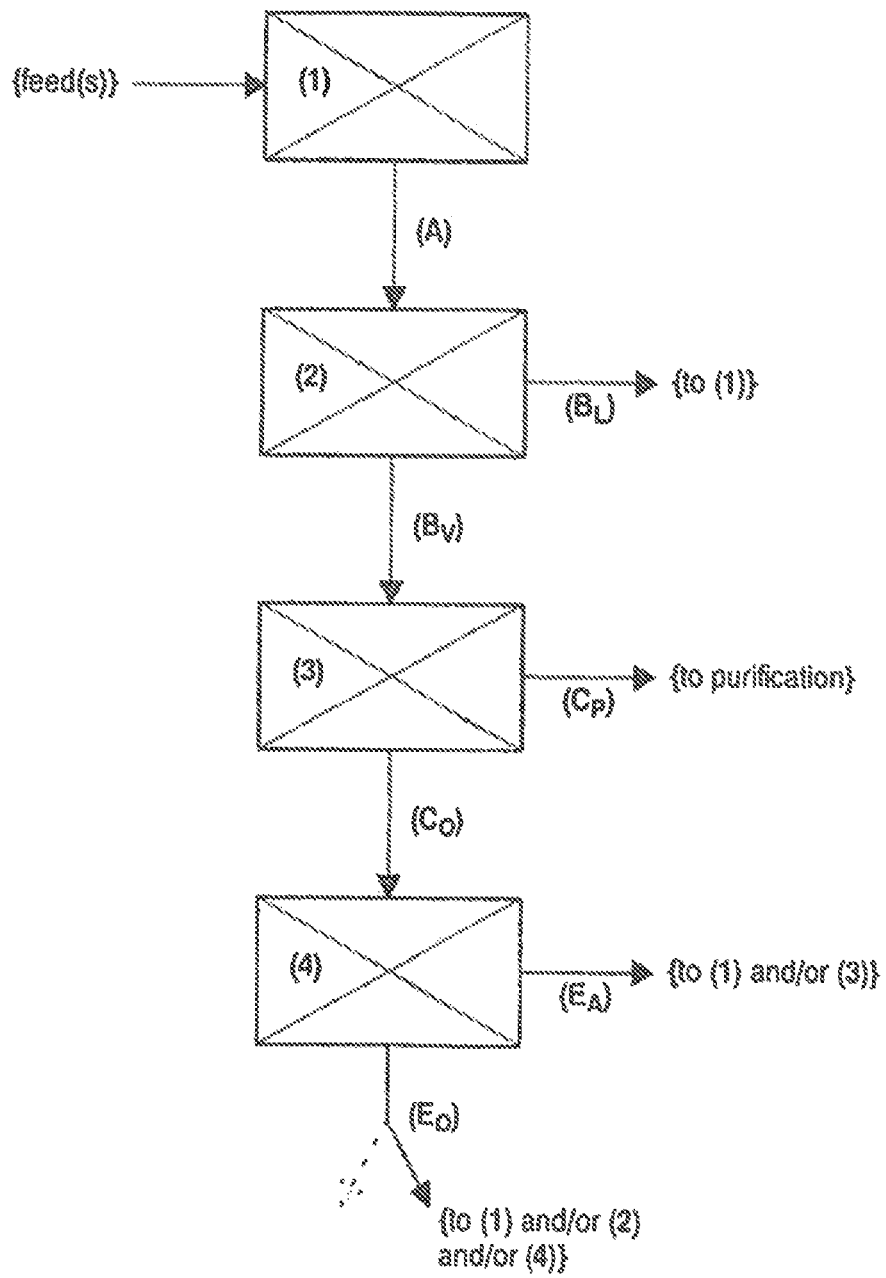
FIG. 1 shows a flowchart that illustrates the flow of the streams involved in the process according to the present disclosure.

A detailed description of embodiments of the present process is disclosed herein. However, it is to be understood that the disclosed embodiments are merely exemplary of the process and that the process may be embodied in various and alternative forms of the disclosed embodiments. Therefore, specific procedural, structural and functional details which are addressed in the embodiments disclosed herein are not to be interpreted as limiting, but merely as a basis for the claims and as a representative basis for teaching one skilled in the art to variously employ the present process.

Unless specifically stated otherwise, all technical terms used herein have the meaning as commonly understood by those skilled in the art.

The designation of groups of the Periodic Table of the Elements as used herein is in accordance with the current IUPAC convention.

Moreover, unless specifically stated otherwise, the following expressions as used herein are understood to have the following meanings.

The expression "liquid stream" as used herein refers to a product or composition which is in the liquid state under the conditions of the processing step in which the stream is formed.

Correspondingly, the expression "vapor stream" as used herein refers to a product or composition which is in the gaseous state under the conditions of the processing step in which the stream is formed.

The expression "reaction zone" as used herein refers to at least one reactor or vessel in which methanol is carbonylated in the presence of a catalyst to form acetic acid at elevated pressure and temperature, i.e., the reactor(s) of a methanol producing plant.

The expression "flash zone" as used herein refers to at least one tank or vessel in which the reaction mixture obtained by carbonylating methanol in the presence of a catalyst to form acetic acid is at least partially depressurized and/or cooled to form a vapor stream and a liquid stream, i.e., the flash tank(s) in the reaction area of a methanol producing plant.

The expression "fractioning zone" as used herein refers to at least one fractioning or distillation column, i.e., the light ends distillation column(s) in the light ends recovery area of an acetic acid producing plant.

In general, the expression "innate" as used herein with in reference to a chemical compound refers to a chemical compound which is introduced to the process as a starting material, or as a constituent of a starting material stream, which is fed to the reaction zone, as well as a chemical compound which is generated in the process as a product or by-product, e.g., of the carbonylation of methanol in the presence of the catalyst, or of a work-up or purification stage.

Correspondingly, the expression "extraneous" as used herein with a view to a chemical compound refers to a chemical compound which is introduced to the process separately and independent from starting material streams that are fed to the reaction zone. The expression "extraneous" in particular also excludes any a chemical compound which is generated in the process as a product or by-product.

Thus, the expression "innate alkane" and the plural thereof as used herein refers to one or more alkanes which are introduced to the process as a constituent of a starting material stream, e.g., the carbon monoxide and methanol feed streams, as well as alkanes which may be generated in the process as a by-product or by-products, e.g., of the carbonylation of methanol in the presence of the catalyst, or of a work-up or purification stage.

The expression "extraneous alkane" and the plural thereof as used herein refer to one or more alkanes which are introduced to the process separately and independent from starting material streams that are fed into the reaction zone. The expression "extraneous alkane" and the plural thereof in particular also exclude alkanes which may be generated in the process.

The expression "innate water" as used herein refers to water which is introduced to the process as a starting material or as a constituent of a starting material feed stream, e.g., carbon monoxide and methanol feed streams, as well as water which is generated in the process, e.g., as a by-product via the water-gas shift reaction.

Correspondingly, the expression "extraneous water" as used herein refers to water which is introduced to the process separately and independent from starting material streams that are fed into the reaction zone. The expression "extraneous water" in particular also excludes water which may be generated in the process.

Unless specifically indicated otherwise, the expression "heavy phase" refers to the organic, methyl iodide containing phase as, e.g., obtained in the decanter operation of an acetic acid plant. The expression in particular includes the heavy, organic phase ($D_O$) in accordance with this disclosure.

The expressions "OAc" or "AcO" are used herein as abbreviations for the acetate anion, i.e., $H_3CC(=O)O^-$.

The expression "Me" is used herein as an abbreviation for the methyl group.

The expression "acac" is used herein as an abbreviation for acetoacetate anion, i.e., $H_3CC(=O)CH_2C(=O)O^-$.

Unless specifically indicated otherwise, the expression "wt. %" as used herein refers to the percentage by weight of a particular component in the referenced composition.

With respect to all ranges disclosed herein, such ranges are intended to include any combination of the mentioned upper and lower limits even if the particular combination is not specifically listed.

All publications, patent applications, and patents mentioned herein are incorporated by reference in their entirety. In the event of conflict, the present specification, including definitions, is intended to control.

One aspect of the present disclosure provides for a process for producing acetic acid which involves (a) carbonylating methanol in the presence of a catalyst in a reaction zone to obtain a reaction mixture (A) comprising acetic acid, methyl acetate, methyl iodide, the catalyst, and water;

(b) separating at least a part of the reaction mixture (A) in a flash zone to obtain a liquid stream (BO comprising the catalyst, and a vapor stream ($B_V$) comprising acetic acid, methyl acetate, methyl iodide, and water;

(c) separating the vapor stream ($B_V$) in a fractioning zone to obtain a product stream (Cp) comprising acetic acid and a minor amount of water, and an overhead stream ($C_O$) comprising acetic acid, methyl acetate, methyl iodide, and water;

(d) condensing the overhead stream ($C_O$) and forming a liquid mixture (D) which has a water content of at most 20% by weight, based on the weight of the liquid mixture, and a weight ratio of acetic acid to water of at least 1:1, and (e) partitioning the liquid mixture (D) by providing for an alkane(s) content of D of from 0.1 to 15% by weight, based on the weight of D, to obtain a light, aqueous phase ($D_A$) comprising acetic acid and water, and a heavy, organic phase ($D_O$) comprising methyl iodide, methyl acetate, and the alkane(s).

Alkanes have been observed as by-products in the carbonylation of methanol under conventional conditions which maintain a water concentration in the reaction mixture of approximately 14 or 15 wt. %. In those processes, however, the phase separation of the condensed overhead stream recovered from the light ends distillation occurs due to the relatively high water content and low acid content of the overhead stream.

Surprisingly, it has been found that the condensed overhead stream ($C_O$) which is obtained when acetic acid is produced by carbonylating methanol under low water-high acid conditions can be efficiently and thoroughly separated into an aqueous phase ($D_A$) and an organic phase ($D_O$) by forming a liquid mixture (D) which has an alkanes content of from 0.1 to 15% by weight, based on the weight of D. Further, it has surprisingly been found that the efficient phase separation in the decanter of an acetic acid plant can be maintained stable by maintaining a sufficient amount of innate or extraneous alkanes in the reaction mixture. The process, therefore, not only facilitates the phase separation in the decanter but also simplifies the removal of by-products from the process.

Figure 2:
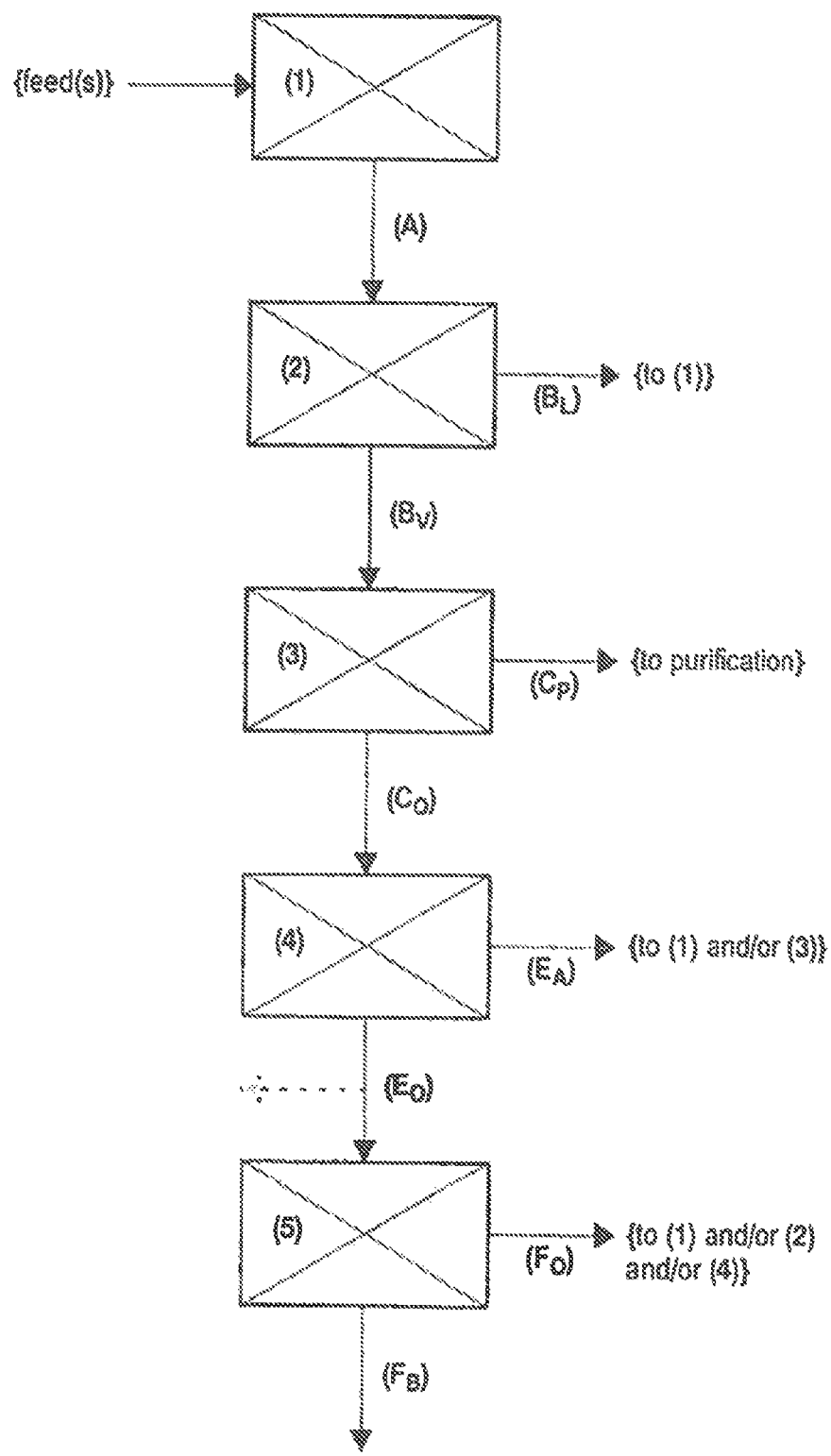
FIG. 2 shows a flowchart that illustrates the flow of the streams involved in the process according to the present disclosure.

The flowcharts in FIGS. 1 and 2 schematically illustrate the flow of the streams involved in the process of the present disclosure. Accordingly, the starting materials are fed continuously or batch-wise into the reaction zone (1). At least a part of the reaction mixture (A) which is formed in the reaction zone (1) is withdrawn and is separated, by a flash separation in the flash zone (2), to obtain a liquid stream ($B_L$) comprising the catalyst and, where present, the catalyst stabilizer, and a vapor stream ($B_V$) comprising the acetic acid, methyl acetate, methyl iodide, and water. The liquid stream ($B_L$) is preferably recycled to the reaction zone (1).

The vapor stream ($B_V$) is conveyed to the fractioning zone (3) where it is separated to obtain at least a product stream ($C_P$) comprising acetic acid and a minor amount of water, and an overhead stream ($C_O$) comprising acetic acid, methyl acetate, methyl iodide, and water. Those having ordinary skill will appreciate that further streams (not shown) may be recovered from the fractioning zone (3), e.g., a bottoms stream ($C_B$) comprising any catalyst which may have become entrained in $B_V$. Where applicable, such bottoms stream ($C_B$) may be recycled to the reaction zone (1) (not shown).

The overhead stream ($C_O$) is condensed and a liquid mixture (D) is formed which has a water content of at most 20% by weight, based on the weight of the liquid mixture, and a weight ratio of acetic acid to water of at least 1:1. The liquid mixture (D) is partitioned in a separation vessel (4), i.e., a decanter, by providing for an alkane(s) content of D of from 0.1 to 15% by weight, based on the weight of D, to obtain a light, aqueous phase ($D_A$) comprising acetic acid and water, and a heavy, organic phase ($D_O$) comprising methyl iodide, methyl acetate, and the alkane(s).

The partitioned phases $D_A$ and $D_O$ are separated to obtain an aqueous stream ($E_A$) and an organic stream ($E_O$).

The aqueous stream ($E_A$) may be recycled, in whole or in part, to the reaction zone (1) and/or the fractioning zone (3). Preferably, the aqueous stream ($E_A$), or a part thereof, which is being recycled is processed to remove impurities and excess water before being reintroduced into the process. Suitable processing methods are known in the art and include, e.g., the methods disclosed in U.S. Pat. No. 5,625,095, U.S. Pat. No. 5,783,731, U.S. Pat. No. 6,143,930, and U.S. Pat. No. 6,339,171. The organic stream ($E_O$) may be recycled, in whole or in part, to the reaction zone (1), the flash zone (2), and/or the separation zone (4).

In accordance with the embodiments schematically illustrated in the flow chart FIG. 2, at least a part of the organic stream ($E_O$) is further separated in a distillation zone (5) to obtain an overhead product ($F_O$) comprising methyl iodide and at least a part of the alkanes, and a bottom product ($F_B$) comprising acetic acid, methyl acetate, water, and optionally an additional part of the alkanes. The overhead product ($F_O$) may be recycled to the reaction zone (1), the flash zone (2), and/or the separation zone (4). The bottom product ($F_B$) may be purged from the process to maintain the water balance of the reaction system, or may be treated further to remove excess water and/or impurities before being recycled to the reaction zone (1), the flash zone (2), and/or the separation zone (4) (not shown).

While the process may be performed batch-wise, it is preferable to operate the process continuously.

The carbonylation reaction in accordance with the present disclosure is performed in the presence of a carbonylation catalyst and optionally a catalyst stabilizer. Suitable carbonylation catalysts include those known in the acetic acid industry. Examples of suitable carbonylation catalysts include rhodium catalysts and iridium catalysts.

Suitable rhodium catalysts are described, for example, in U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_2$, the like, and mixtures thereof.

Suitable iridium catalysts are described, for example, in U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $I_N(CO)_{12}$, $IrCl_3 \times 4H_2O$, $IrBr_3 \times 4H_2O$, $Ir_3(CO)_{12}$, $Ir_2O_3$, $IrO_2$, $Ir(acac)(CO)_2$, $Ir(acac)_3$, $Ir(OAc)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are acetates.

The reaction rate depends upon the concentration of the catalyst in the reaction mixture (A). The catalyst concentration normally is from about 1.0 mmol to about 100 mmol catalyst per liter (mmol/l) of (A). In some embodiments, the catalyst concentration is at least 2.0 mmol/l, or at least 5.0 mmol/l, or at least 7.5 mmol/l. In some embodiments the catalyst concentration is at most 75 mmol/l, or at most 50 mmol/l, or at least 25 mmol/l. In particular embodiments, the catalyst concentration is from about 2.0 to about 75 mmol/l, or from about 2.0 to about 50 mmol/l, or from about 5.0 to about 25 mmol/l.

In some embodiments, the reaction is performed in the presence of a catalyst stabilizer. Suitable catalyst stabilizers include those known to the industry. In general, there are two types of catalyst stabilizers. The first type of catalyst stabilizer is metal iodide salt, i.e., a iodide of a metal of Group 1 or 2 such as lithium iodide. The second type of catalyst stabilizer is a non-salt stabilizer. Preferred non-salt stabilizers are pentavalent Group 15 oxides. See U.S. Pat. No. 5,817,869. Phosphine oxides are more preferred. Triphenylphosphine oxides are most preferred.

The amount of metal iodide, when used, generally is such that a concentration of from about 1 to about 20 wt. % (about 0.1 to about 1.75 M) of the metal iodide is present in the reaction mixture. More preferably, this optional component is present in the reaction mixture in an amount of from about 5 to about 10 wt. % which corresponds to a molarity range of from about 0.5 to about 1.0 M.

The amount of pentavalent Group 15 oxide, when used, generally is such that its concentration to rhodium is greater than about 60:1. Preferably, the concentration of the pentavalent Group 15 oxide to rhodium is from about 60:1 to about 500:1. In some embodiments, from about 0.1 to about 3 M of the pentavalent Group 15 oxide is present in the reaction mixture. More preferably, from about 0.15 to about 1.5 M, or from 0.25 to 1.2 M, of the pentavalent Group 15 oxide is present in the reaction mixture.

The carbonylation reaction is performed in the presence of a finite amount of water. Preferably, the concentration of water which is present in the reaction mixture (A) amounts to not more than about 10 wt. % based on the total weight of the reaction mixture (A). More preferably, the water concentration is at most 6 wt. %, or at most 4 wt. %, or at most 2 wt. %. In some embodiments, the concentration of water in the reaction mixture is at least 0.1 wt. %, or at least 0.5 wt. %, or at least 1 wt. %. Accordingly, the water concentration in the reaction mixture may range from 0.1 to 10 wt. %, or from 0.1 to 6 wt. %, or from 0.1 to 4 wt. %, or from 0.1 to 2 wt. %. Alternatively, the water concentration in the reaction mixture may range from 0.5 to 10 wt. %, or from 0.5 to 6 wt. %, or from 0.5 to 4 wt. %, or from 0.5 to 2 wt. %. Similarly, the water concentration in the reaction mixture may range from 1 to 10 wt. %, or from 1 to 6 wt. %, or from 1 to 4 wt. %, or from 1 to 2 wt. %.

The reaction is preferably performed in the presence of methyl acetate as a rate promoter. Methyl acetate may be formed in situ. Normally, methyl acetate may be added as a starting material to the reaction mixture. Preferably, the concentration of methyl acetate in the reaction mixture (A) may be from about 2 wt. % to about 20 wt. % based on the total weight of the reaction mixture (A). More preferably, the concentration of methyl acetate may be from about 2 wt. % to about 16 wt. %. Most preferably, the concentration of methyl acetate is from about 2 wt. % to about 8 wt. %. Alternatively, methyl acetate or a mixture of methyl acetate and methanol from by-product streams of the hydrolysis/methanolysis of polyvinyl acetate can be used for the carbonylation reaction.

The reaction is performed in the presence of methyl iodide. Methyl iodide acts as a catalyst promoter. Preferably, the concentration of methyl iodide is from about 0.6 wt. % to about 36 wt. % based on the total weight of the reaction mixture (A). More preferably, the concentration of methyl iodide is from about 4 wt. % to about 24 wt. %. Most preferably, the concentration of methyl iodide is from about 6 wt. % to about 20 wt. %. Alternatively, methyl iodide can be generated in the carbonylation reactor or reaction zone (1) by adding hydrogen iodide.

Hydrogen may also be fed into the reaction zone (1). Addition of hydrogen can enhance the carbonylation efficiency. Preferably, the concentration of hydrogen is from about 0.1 mol % to about 5 mol % of carbon monoxide in the reaction zone (1). More preferably, the concentration of hydrogen is from about 0.3 mol % to about 3 mol % of carbon monoxide in the reaction zone (1).

Methanol and carbon monoxide are fed to the reaction zone (1). The methanol feed to the carbonylation reaction can come from a syngas-methanol facility or any other source. Methanol does not react directly with carbon monoxide to form acetic acid. It is converted to methyl iodide by the hydrogen iodide present in the reaction zone (1) and then reacts with carbon monoxide and water to give acetic acid and regenerate hydrogen iodide. Carbon monoxide not only becomes part of the acetic acid molecule, but it also plays an important role in the formation and stability of the active catalyst.

The carbonylation reaction is preferably performed at a temperature of about 120° C. to about 250° C. More preferably, the reaction is performed at a temperature of about 150° C. to about 200° C.

The carbonylation reaction is preferably performed under a pressure of about 200 psig to about 2,000 psig. More preferably, the reaction is performed under a pressure of about 300 psig to about 500 psig.

The flash zone (2) is preferably maintained at a pressure below that of the reaction zone (1), typically at a pressure of from about 10 to 100 psig. The flash zone (2) is preferably maintained at a temperature of from about 100 to 160° C.

The vapor stream ($B_V$) comprising the acetic acid, methyl iodide, and water, is conveyed from the flash zone (2) to the fractioning zone (3) where it is separated to obtain a product stream ($C_P$) comprising acetic acid and a minor amount of water, and an overhead stream ($C_O$) comprising acetic acid, methyl acetate, methyl iodide, and water. The product stream ($C_P$) is normally subjected to further purification in a manner known per se.

The fractioning zone (3) is normally embodied by one or more distillation columns. Those having ordinary skill in the art will readily appreciate that the temperature and pressure conditions maintained in the fractioning zone (3) will depend upon the number and type of distillation columns, and on the distillation stages of the column or columns. Illustratively, when the fractioning zone (3) is embodied by one distillation column, the column preferably has at least 10, more preferably at least 14, or at least 18, actual stages. In such a set-up, the distillation column is preferably operated at an overhead pressure within the range of 20 psia (1.4 kg/cm$^2$) to 40 psia (2.8 kg/cm$^2$), or from 25 to 35 psia, and at a bottom pressure of 25 from psia to 45 psia, or from 30 psia to 40 psia. Correspondingly, the overhead temperature is of from 95° C. to 135° C., or from 100° C. to 125° C., or from 110° C. to 120° C., and the bottom temperature is of from 115° C. to 155° C., or from 125° C. to 135° C.

The overhead stream ($C_O$) is recovered from the fractioning zone (3) and is condensed in a manner known per se, e.g., by cooling.

In some embodiments of the process, the overhead stream ($C_O$) may have a water content of at most 17 wt. %, or at most 15 wt. %, or at most 12 wt. %, or at most 10 wt. %, or at most 7 wt. %. Generally, the overhead stream ($C_O$) has a water content of at least 0.5 wt. %, or at least 1 wt. %, or at least 2 wt. %, or at least 5 wt. %. In particular embodiments, the water content of the overhead stream ($C_O$) may range from 0.5 wt. % to 20 wt. %, or from 0.5 wt. % to 17 wt. %, or from 0.5 wt. % to 15 wt. %, or from 0.5 wt. % to 12 wt. %, or from 0.5 wt. % to 10 wt. %, or from 0.5 wt. % to 7 wt. %. In other embodiments, the water content of the overhead stream ($C_O$) may range from 1 wt. % to 20 wt. %, or from 1 wt. % to 17 wt. %, or from 1 wt. % to 15 wt. %, or from 1 wt. % to 12 wt. %, or from 1 wt. % to 10 wt. %, or from 1 wt. % to 7 wt. %. In other embodiments, the water content of the overhead stream ($C_O$) may range from 2 wt. % to 20 wt. %, or from 2 wt. % to 17 wt. %, or from 2 wt. % to 15 wt. %, or from 2 wt. % to 12 wt. %, or from 2 wt. % to 10 wt. %, or from 2 wt. % to 7 wt. %. In yet further embodiments, the water content of the overhead stream ($C_O$) may range from 5 wt. % to 20 wt. %, or from 5 wt. % to 17 wt. %, or from 5 wt. % to 15 wt. %, or from 5 wt. % to 12 wt. %, or from 5 wt. % to 10 wt. %, or from 5 wt. % to 7 wt. %.

In some embodiments of the process, the weight ratio of acetic acid to water in the overhead stream ($C_O$) is at least 1.5:1, or at least 3:1, or at least 5:1, or at least 10:1.

In general, the overhead stream ($C_O$) may have an acetic acid content of at least 5 wt. %, or at least 7 wt. %, or at least 10 wt. %, or at least 15 wt. %. Normally, the acetic acid content of the overhead stream ($C_O$) will not exceed 35 wt. %, or 30 wt. %, or 25% wt. %. Accordingly, the acetic acid content of the overhead stream ($C_O$) may range from 5 to 35 wt. %, or from 7 to 35 wt. %, or from 10 to 35 wt. %, or from 15 to 35 wt. %. Alternatively, the acetic acid content of the overhead stream ($C_O$) may range from 5 to 30 wt. %, or from 7 to 30 wt. %, or from 10 to 30 wt. %, or from 15 to 30 wt. %. Further, the acetic acid content of the overhead stream ($C_O$) may range from 5 to 25 wt. %, or from 7 to 25 wt. %, or from 10 to 25 wt. %, or from 15 to 25 wt. %.

The concentration of methyl acetate in the overhead stream ($C_O$) normally will be at most 20 wt. %, or at most 15 wt. %, or at most 12 wt. %, or at most 10 wt. %, and generally will be not less than 1.5 wt. %, or 4 wt. %, or 6 wt. %. Accordingly, methyl acetate concentration in the overhead stream ($C_O$) may range from 1.5 to 20 wt. %, or from 1.5 to 15 wt. %, or from 1.5 to 12 wt. %, or from 1.5 to 10 wt. %. Correspondingly, methyl acetate concentration in the overhead stream ($C_O$) may range from 4 to 20 wt. %, or from 4 to 15 wt. %, or from 4 to 12 wt. %, or from 4 to 10 wt. %. Alternatively, methyl acetate concentration in the overhead stream ($C_O$) may range from 6 to 20 wt. %, or from 6 to 15 wt. %, or from 6 to 12 wt. %, or from 6 to 10 wt. %.

Methyl iodide is present in the overhead stream ($C_O$) generally in at least 30 wt. %, or at least 40 wt. %, or at least 45 wt. %, or at least 50 wt. %, and normally will not exceed 93 wt. %, or 90 wt. %, or 75 wt. %. Accordingly, the methyl iodide concentration of the overhead stream (Co) may range from 30 to 93 wt. %, or from 40 to 93 wt. %, or from 45 to 93 wt. %, or from 50 to 93 wt. %. Correspondingly, the methyl iodide concentration of the overhead stream ($C_O$) may range from 30 to 90 wt. %, or from 40 to 90 wt. %, or from 45 to 90 wt. %, or from 50 to 90 wt. %. Alternatively, the methyl iodide concentration of the overhead stream ($C_O$) may range from 30 to 75 wt. %, or from 40 to 75 wt. %, or from 45 to 75 wt. %, or from 50 to 75 wt. %.

Those having skill in the art will appreciate that the overhead stream ($C_O$) additionally may comprise normally gaseous constituents such as hydrogen, carbon monoxide and carbon dioxide, as well as carbonyl components which are formed as by-products of the reaction. Non-condensable, normally gaseous constituents of the overhead stream ($C_O$) may be vented (not shown).

The process of the present disclosure entails forming a liquid mixture (D) which has a water content of at most 20% by weight, based on the weight of the liquid mixture, and a weight ratio of acetic acid to water of at least 1:1. Preferably, the water which is present in the liquid mixture (D) exclusively is innate water. The liquid mixture (D) may be formed prior to, during, or after condensation of the overhead stream ($C_O$), prior to or during conveying the condensed overhead stream ($C_O$) to the separation zone (4), or in the separation zone (4). As the phase separation time and the residence time of the mixture in the separation zone (4) preferably be low, it is generally preferable to form the liquid mixture (D) prior to, during, or after condensation of the overhead stream ($C_O$), prior to or during conveying the condensed overhead stream ($C_O$) to the separation zone (4).

In accordance with some embodiments, the liquid mixture (D) is formed by adding to $C_O$ one or more extraneous or innate alkanes, methyl iodide, acetic acid, or mixtures thereof, optionally in combination with innate water, provided that the resultant composition of D contains at most 20% by weight of water and contains acetic acid and water in a weight ratio of at least 1:1. Suitable sources for innate alkanes, methyl iodide, acetic acid, or mixtures thereof, optionally in combination with innate water, include for example, the streams $E_A$ and $E_O$, and preferably $F_O$. When providing the alkanes content of the liquid mixture (D) based on innate alkanes, the suitable concentration of alkanes in D conveniently is adjusted by controlling the amount of $E_O$ and $F_O$, respectively, which is combined with $C_O$, and/or by controlling the amount of $E_O$ which is conveyed to the distillation zone (5). In particular embodiments of the continuous procedure, the amounts and the concentration of the recycle streams $E_O$ and $F_O$ are controlled such as to establish a steady state concentration of alkanes in $C_O$ of from about 0.1 to 15 wt. %, based on the weight of the $C_O$ condensate. Thus, under steady state conditions, the liquid mixture (D) is formed by condensing $C_O$.

The extraneous or innate alkanes which are provided in the liquid mixture preferably have at least 5, or at least 6 carbon atoms, and may be straight chain, branched or cyclic. The alkanes may be employed as a pure compound or as a mixture of isomers and/or as a mixture of alkanes having different amounts of carbon atoms. Those of ordinary skill will appreciate that the number of carbon atoms of the alkane(s), or the boiling point thereof; is of subsidiary relevance with a view to the effect of the alkane(s) on the phase separation. Accordingly, the nature of the alkane(s) may vary broadly.

In some embodiments of the process, especially when it is desired to recycle the alkane(s) to the reaction zone, the flash zone, or the fractioning zone, it may be advantageous to adjust the alkane(s) fraction such that sufficient amounts thereof reach the overhead stream ($C_O$). Suitable alkane(s) fractions, for example, may have a boiling point of at least about 40° C., or at least about 50° C., or at least about 60° C. Moreover, suitable alkane(s) fractions may have a boiling point of at most about 130° C., or at most about 125° C., or at most about 120° C., or at most about 115° C. Accordingly, the boiling point or boiling range of the innate or extraneous alkanes and the mixtures thereof may range from about 40 to about 130° C., or from about 40 to about 125° C., or from about 40 to about 120° C., or from about 40 to about 115° C. Alternatively, the boiling point or boiling range of the innate or extraneous alkanes and the mixtures thereof may range from about 50 to about 130° C., or from about 50 to about 125° C., or from about 50 to about 120° C., or from about 50 to about 115° C. Moreover, the boiling point or boiling range of the innate or extraneous alkanes and the mixtures thereof may range from about 60 to about 130° C., or from about 60 to about 125° C., or from about 60 to about 120° C., or from about 60 to about 115° C. Those having ordinary skill will appreciate that the suitable alkane(s) fractions may include minor amounts of alkanes having a boiling point outside of the specified ranges, i.e., a boiling point>130° C. Such minor amounts normally will be no more than 10 mole percent, or no more than 7 mole percent, or no more than 5 mole percent.

In other embodiments, especially when it is desired to recycle the alkane(s) from the distillation zone (5) to the separated overhead stream ($C_O$), prior to or during condensation, or to the separation zone (4), the boiling point or boiling range of the alkane(s) fraction may be in the above delineated ranges or may be advantageous to employ an alkane(s) fraction having a boiling point or boiling range above 130° C.

When extraneous alkanes are employed, the extraneous alkane(s) may be added to $C_O$ either batch-wise or continuously. In some embodiments, the alkane(s) will be added batch-wise throughout the process. In other embodiments, the alkane(s) will be added continuously until the desired steady state concentration of alkane(s) in $C_O$ is established, and will be added continuously or batch-wise thereafter.

The liquid mixture (D) which is obtained in this manner is partitioned in the decanter (4) into a light, aqueous phase ($D_A$) comprising acetic acid and water, and a heavy, organic phase ($D_O$) comprising methyl iodide, methyl acetate, and the alkane(s).

The presence of the alkane(s) in the liquid mixture (D) in accordance with the present disclosure causes the phase separation of D or at least expedites it. While not wishing to be bound by theory, it is currently believed that the alkanes reduce the polarity of the organic phase and, thus, significantly decrease the solubility of acetic acid in the heavy phase. As the amount of acetic acid which is soluble in the organic phase decreases, the polarity of the organic phase is further reduced. As a result, the amounts in which water and acetic acid are soluble in the organic phase are reduced below the amounts of acetic acid and water present in the mixture (D) and phase separation occurs. Also, as the alkane(s) reduce the polarity of the organic phase, the concentration of methyl iodide and of methyl acetate in the organic phase increases. As a result, the aqueous phase becomes more depleted in methyl iodide and methyl acetate than is the case in the absence of the alkane(s). It has been observed that the presence of the alkane(s) even in minor amounts, i.e., about 0.1 wt. %, may be sufficient to reduce the time necessary for phase separation of the mixture (D) by more than 50%. On the other hand, when the alkane(s) content of the mixture (D) is increased beyond a certain limiting concentration, i.e., 15 wt. %, the time necessary for phase separation of the mixture (D) again increases and phase separation may be hindered, or even be prevented, when the alkane(s) concentration is further increased. While not wishing to be bound by theory, it is currently believed that the concentration of the alkane(s) in the mixture (D) at which phase separation is hindered or may even be prevented depends on the density of the organic phase and, thus, on the ratio of alkane(s) to methyl iodide, as well as the amount of methyl acetate which is present in the mixture (D). The density of an admixture of methyl iodide and alkane(s) decreases with increasing alkane(s) content and a similar effect can be expected when methyl acetate is added. Accordingly, as the ratio of alkanes to methyl iodide, and/or the total amount of methyl acetate in the mixture (D) increases, the density of a phase formed by the alkane(s), the methyl iodide and the methyl acetate may be reduced to a point where the density differential between the organic phase and the aqueous phase becomes insufficient to promote the gravity governed phase separation.

Thus, the alkane(s) concentration in the liquid mixture (D) should be at least 0.1 wt. % and at most 15 wt. %. It will be appreciated by those of ordinary skill that the concentration of alkane(s) which provides optimum phase separation for a specific liquid mixture (D) will depend on factors such as the amount of methyl iodide and the amount of methyl acetate which is present in the liquid mixture. More specifically, the optimum alkane(s) concentration may tend to be at the higher end of the range when the methyl iodide concentration of (D) is high and/or the methyl acetate concentration of (D) is low. On the other hand, the optimum alkane(s) concentration may tend to be at the lower end of the range when the methyl iodide concentration of (D) is low and/or the methyl acetate concentration is high.

Accordingly, in addition to adjusting the alkane(s) concentration in the liquid mixture (D), creating optimum conditions for phase separating the liquid mixture (D) may involve increasing the concentration of methyl iodide in the liquid mixture and thereby reducing the concentration of methyl acetate. The methyl iodide employed for this purpose may be extraneous or innate. Suitable sources for innate methyl iodide are in particular the streams $E_O$ and $F_O$, preferably $F_O$. Additionally, where the process is run under continuous conditions, a part of the stream feeding methyl iodide into the reaction zone (1) may be split off and may serve as an extraneous source of methyl iodide for the liquid mixture (D). This approach may be employed prior to, during, or after the phase of the continuous process in which the steady state concentration of alkane(s) in $C_O$ is being established.

The exact composition of the liquid mixture (D) generally may vary so long as the water content does not exceed 20 wt. %, the weight ratio of acetic acid to water is at least 1:1, and the alkane(s) concentration is from 0.1 to 15 wt. %.

In some embodiments of the process, the liquid mixture (D) may have a water content of at most 17 wt. %, or at most 15 wt. %, or at most 12 wt. %, or at most 10 wt. %, or at most 7 wt. %. Generally, the liquid mixture (D) has a water content of at least 0.5 wt. %, or at least 1 wt. %, or at least 2 wt. %, or at least 5 wt. %. In particular embodiments, the water content of the liquid mixture (D) may range from 0.5 wt. % to 20 wt. %, or from 0.5 wt. % to 17 wt. %, or from 0.5 wt. % to 15 wt. %, or from 0.5 wt. % to 12 wt. %, or from 0.5 wt. % to 10 wt. %, or from 0.5 wt. % to 7 wt. %. In other embodiments, the water content of the liquid mixture (D) may range from 1 wt. % to 20 wt. %, or from 1 wt. % to 17 wt. %, or from 1 wt. % to 15 wt. %, or from 1 wt. % to 12 wt. %, or from 1 wt. % to 10 wt. %, or from 1 wt. % to 7 wt. %. In other embodiments, the water content of the liquid mixture (D) may range from 2 wt. % to 20 wt. %, or from 2 wt. % to 17 wt. %, or from 2 wt. % to 15 wt. %, or from 2 wt. % to 12 wt. %, or from 2 wt. % to 10 wt. %, or from 2 wt. % to 7 wt. %. In yet further embodiments, the water content of the liquid mixture (D) may range from 5 wt. % to 20 wt. %, or from 5 wt. % to 17 wt. %, or from 5 wt. % to 15 wt. %, or from 5 wt. % to 12 wt. %, or from 5 wt. % to 10 wt. %, or from 5 wt. % to 7 wt. %.

In some embodiments of the process, the weight ratio of acetic acid to water in the liquid mixture (D) is at least 1.5:1, or at least 3:1, or at least 5:1, or at least 10:1.

Generally, the alkanes content of the liquid mixture (D) is at most 15 wt. %, or at most 13 wt. %, or at least 11.5 wt. %, or at least 10 wt. %. In some embodiments of the process, the alkanes content of the liquid mixture (D) is at least 0.25 wt. %, or at least 0.5 wt. %, or at least 1.0 wt. %, or at least 2.0 wt. %. In particular embodiments, the water content of the liquid mixture (D) may range from 0.1 to 15 wt. %, or from 0.25 to 15 wt. %, or from 0.5 to 15 wt. %, or from 1.0 to 15 wt. %, or from 2.0 to 15 wt. %. In further particular embodiments, the water content of the liquid mixture (D) may range from 0.1 to 13 wt. %, or from 0.25 to 13 wt. %, or from 0.5 to 13 wt. %, or from 1.0 to 13 wt. %, or from 2.0 to 13 wt. %. In yet other particular embodiments, the water content of the liquid mixture (D) may range from 0.1 to 11.5 wt. %, or from 0.25 to 11.5 wt. %, or from 0.5 to 11.5 wt. %, or from 1.0 to 11.5 wt. %, or from 2.0 to 11.5 wt. %. In additional embodiments, the water content of the liquid mixture (D) may range from 0.1 to 10 wt. %, or from 0.25 to 10 wt. %, or from 0.5 to 10 wt. %, or from 1.0 to 10 wt. %, or from 2.0 to 10 wt. %.

Methyl iodide is present in the liquid mixture (D) generally in at least 30 wt. %, or at least 40 wt. %, or at least 45 wt. %, or at least 50 wt. %, and normally will not exceed 93 wt. %, or 90 wt. %, or 75 wt. %. Accordingly, the methyl iodide concentration of the liquid mixture (D) may range from 30 to 93 wt. %, or from 40 to 93 wt. %, or from 45 to 93 wt. %, or from 50 to 93 wt. %. Correspondingly, the methyl iodide concentration of the liquid mixture (D) may range from 30 to 90 wt. %, or from 40 to 90 wt. %, or from 45 to 90 wt. %, or from 50 to 90 wt. %. Alternatively, the methyl iodide concentration of the liquid mixture (D) may range from 30 to 75 wt. %, or from 40 to 75 wt. %, or from 45 to 75 wt. %, or from 50 to 75 wt. %.

In particular embodiments the weight ratio of methyl iodide to the alkane(s) in the liquid mixture (D) is at least 3:1, or is at least 4:1, or is at least 5:1. Particular embodiments also include those where the weight ratio of methyl iodide to the alkane(s) in the liquid mixture (D) is at most 800:1, or at most 650:1, or at most 500:1. Accordingly, the weight ratio of methyl iodide to the alkane(s) in the liquid mixture (D) in particular embodiments may range from 3:1 to 800:1, or from 4:1 to 800:1, or from 5:1 to 800:1. Correspondingly, the weight ratio of methyl iodide to the alkane(s) in the liquid mixture (D) in particular embodiments may range from 3:1 to 650:1, or from 4:1 to 650:1, or from 5:1 to 650:1. Alternatively, the weight ratio of methyl iodide to the alkane(s) in the liquid mixture (D) in particular embodiments may range from 3:1 to 500:1, or from 4:1 to 500:1, or from 5:1 to 500:1.

The weight ratio of methyl iodide to methyl acetate in the liquid mixture (D) preferably is at least 2.5:1, or is at least 3:1, or is at least 4:1. Particular embodiments also include those where the weight ratio of methyl iodide to methyl acetate in the liquid mixture (D) is at most 600:1, or at most 450:1, or at most 350:1. Accordingly, the weight ratio of methyl iodide to methyl acetate in the liquid mixture (D) in particular embodiments may range from 2.5:1 to 600:1, or from 3:1 to 600:1, or from 4:1 to 600:1. Correspondingly, the weight ratio of methyl iodide to methyl acetate in the liquid mixture (D) in particular embodiments may range from 2.5:1 to 450:1, or from 3:1 to 450:1, or from 4:1 to 450:1. Alternatively, the weight ratio of methyl iodide to methyl acetate in the liquid mixture (D) in particular embodiments may range from 2.5:1 to 350:1, or from 3:1 to 350:1, or from 4:1 to 350:1.

In a particular implementation of the process, at least a part of the organic stream ($E_O$) is separated to obtain an overhead product ($F_O$) comprising methyl iodide and at least a part of the alkanes, and a bottom product ($F_B$) comprising acetic acid, methyl acetate, water and optionally an additional part of the alkanes, and the overhead product ($F_O$) is recycled to the reaction zone (1). Advantageously, the amount of the organic stream ($E_O$) and the separation thereof may be adjusted such as to provide a steady state alkanes content of $C_O$ at the desired level.

The separation of the organic stream ($E_O$) is effected in the distillation zone (5). The distillation zone (5) is normally embodied by one or more distillation columns. Those having ordinary skill in the art will appreciate that the temperature and pressure conditions maintained in the distillation zone (5) will depend upon the number and type of the distillation columns, and on the distillation stages of the column or columns. It will also be appreciated that the bottom and overhead temperature of the distillation(s) may be adjusted to allow an appropriate amount of the alkane(s) which are present in the organic stream ($E_O$) to distill off with the methyl iodide. The manner of adjusting the pertinent parameters such as reflux ratio and temperature is well known in the art. For example, the closer the overhead temperature of the distillation to the boiling point of methyl iodide, the less the amount of alkane(s) will be present in the overhead product ($F_O$). Appropriate distillation conditions for a particular system can be determined by routine experimentation.

A further aspect of the present disclosure employs the principles addressed in the foregoing and provides for a method of expediting phase separation of a mixture comprising acetic acid, methyl iodide, and minor amounts of water, which method comprises providing for an alkanes content of the mixture of from 0.1 to 15% by weight, based on the weight of the mixture.

The method is particularly suited to initiate, or at least improve, the phase separation of mixtures comprising, consisting essentially of or consisting of
  (i) about 40 to 94 wt. % of methyl iodide,
  (ii) about 5 to 40 wt. % of acetic acid, and
  (iii) about 1 to 20 wt. % water,
the weight percentages in each case being based on the total weight of the components (i) to (iii), and wherein the weight ratio of acetic acid (ii) to water (iii) in the mixture is at least 1:1.

In some embodiments, the mixtures to be separated comprise, consist essentially of, or consist of
  (i) about 50 to 90 wt. % of methyl iodide,
  (ii) about 8 to 35 wt. % of acetic acid, and
  (iii) about 2 to 15 wt. % water,
the weight percentages in each case being based on the total weight of the components (i) to (iii), and wherein the weight ratio of acetic acid (ii) to water (iii) in the mixture is at least 1:1.

In further embodiments, the mixtures to be separated comprise, consist essentially of or consist of
  (i) about 60 to 95 wt. % of methyl iodide,
  (ii) about 10 to 30 wt. % of acetic acid, and
  (iii) about 5 to 10 wt. % water,
the weight percentages in each case being based on the total weight of the components (i) to (iii), and wherein the weight ratio of acetic acid (ii) to water (iii) in the mixture is at least 1:1.

Moreover, the method is specifically suited to initiate, or at least improve, the phase separation of mixtures comprising, consisting essentially of, or consisting of
  (i) from 35 to 90% by weight of methyl iodide,
  (ii) from 5 to 35% by weight of acetic acid,
  (iii) from 5 to 15% by weight of water, and
  (iv) up to 15% by weight of methyl acetate,
the weight percentages in each case being based on the total weight of the components (i) to (iv), and wherein the weight ratio of acetic acid to water in the mixture is at least 1:1.

In some embodiments, the mixtures to be separated comprise, consist essentially of or consist of
  (i) from 43 to 85% by weight of methyl iodide,
  (ii) from 5 to 30% by weight of acetic acid,
  (iii) from 5 to 12% by weight of water, and
  (iv) from 5 to 15% by weight of methyl acetate,
the weight percentages in each case being based on the total weight of the components (i) to (iv), and wherein the weight ratio of acetic acid to water in the mixture is at least 1:1.

In further embodiments, the mixtures to be separated comprise, consist essentially of or consist of
  (i) from 52 to 80% by weight of methyl iodide,
  (ii) from 5 to 25% by weight of acetic acid,
  (iii) from 5 to 8% by weight of water, and
  (iv) from 5 to 15% by weight of methyl acetate,
the weight percentages in each case being based on the total weight of the components (i) to (iv), and wherein the weight ratio of acetic acid to water in the mixture is at least 1:1.

In some embodiments of the method, the weight ratio of acetic acid to water in the mixture to be separated is at least 1.5:1, or at least 3:1, or at least 5:1, or at least 10:1.

The alkane(s) which are provided in the mixture to be separated preferably have at least 5, or at least 8, or at least 10 carbon atoms. The alkanes may be straight chain, branched or cyclic, and may be employed as a pure compound or as a mixture of isomers and/or as a mixture of alkanes having different amounts of carbon atoms.

Generally, the alkanes content of the mixture to be separated is at most 15 wt. %, or at most 13 wt. %, or at least 11.5 wt. %, or at least 10 wt. %. In some embodiments of the process, the alkanes content of the mixture to be separated is at least 0.25 wt. %, or at least 0.5 wt. %, or at least 1.0 wt. %, or at least 2.0 wt. %. In particular embodiments, the water content of the mixture to be separated may range from 0.1 to 15 wt. %, or from 0.25 to 15 wt. %, or from 0.5 to 15 wt. %, or from 1.0 to 15 wt. %, or from 2.0 to 15 wt. %. In further particular embodiments, the water content of the mixture to be separated may range from 0.1 to 13 wt. %, or from 0.25 to 13 wt. %, or from 0.5 to 13 wt. %, or from 1.0 to 13 wt. %, or from 2.0 to 13 wt. %. In yet other particular embodiments, the water content of the mixture to be separated may range from 0.1 to 11.5 wt. %, or from 0.25 to 11.5 wt. %, or from 0.5 to 11.5 wt. %, or from 1.0 to 11.5 wt. %, or from 2.0 to 11.5 wt. %. In additional embodiments, the water content of the mixture to be separated may range from 0.1 to 10 wt. %, or from 0.25 to 10 wt. %, or from 0.5 to 10 wt. %, or from 1.0 to 10 wt. %, or from 2.0 to 10 wt. %.

In particular embodiments the weight ratio of methyl iodide to the alkane(s) in the mixture to be separated is at least 3:1, or is at least 4:1, or is at least 5:1. Particular embodiments also include those where the weight ratio of methyl iodide to the alkane(s) in the mixture to be separated is at most 800:1, or at most 650:1, or at most 500:1. Accordingly, the weight ratio of methyl iodide to the alkane(s) in the mixture to be separated in particular embodiments may range from 3:1 to 800:1, or from 4:1 to 800:1, or from 5:1 to 800:1. Correspondingly, the weight ratio of methyl iodide to the alkane(s) in mixture to be separated in particular embodiments may range from 3:1 to 650:1, or from 4:1 to 650:1, or from 5:1 to 650:1. Alternatively, the weight ratio of methyl iodide to the alkane(s) in mixture to be separated in particular embodiments may range from 3:1 to 500:1, or from 4:1 to 500:1, or from 5:1 to 500:1.

The weight ratio of methyl iodide to methyl acetate in the mixture to be separated preferably is at least 2.5:1, or is at least 3:1, or is at least 4:1. Particular embodiments also include those where the weight ratio of methyl iodide to methyl acetate in mixture to be separated is at most 600:1, or at most 450:1, or at most 350:1. Accordingly, the weight ratio of methyl iodide to methyl acetate in the mixture to be separated in particular embodiments may range from 2.5:1 to 600:1, or from 3:1 to 600:1, or from 4:1 to 600:1. Correspondingly, the weight ratio of methyl iodide to methyl acetate in the mixture to be separated) in particular embodiments may range from 2.5:1 to 450:1, or from 3:1 to 450:1, or from 4:1 to 450:1. Alternatively, the weight ratio of methyl iodide to methyl acetate in the mixture to be separated in particular embodiments may range from 2.5:1 to 350:1, or from 3:1 to 350:1, or from 4:1 to 350:1.

The process in accordance with the present disclosure significantly at least improves the quality of phase separation and, in some instances, allows phase separation of mixtures which fail to phase separate without the alkane(s) being present. The quality of the phase separation, thus, is improved at least in that phase separation in accordance with the processes disclosed herein occurs faster than would be the case in the absence of the alkane(s). With a view to the acetic acid production, the reduced time necessary to achieve phase separation decreases the residence time in the decanter and, thus, allows higher recycle rates of the methyl iodide. The higher recycle rates which are made possible by the process in accordance with the present disclosure, in turn, result in a higher steady state concentration of methyl iodide in the reaction zone, thus, allowing for the production of acetic acid to be conducted at higher feed rates.

Additionally, the process in accordance with the present disclosure improves the quality of phase separation in terms of the distribution of acetic acid between the aqueous and the organic phase. With a view to the acetic acid production this means that the amount of the acetic acid which is recycled to the process via the aqueous phase ($D_A$) is increased, whereas the amount of acetic acid which may be removed from the process via the bottom product ($F_B$) is reduced.

The process for producing acetic acid in accordance with the present disclosure therefore allows a more efficient use of starting materials and energy resources.

Moreover, the processes in accordance with the present disclosure significantly improve the reliability of the phase separation. With a view to the acetic acid production, the process prevents that the liquid mixture (D) remains in a single phase, and also prevents that the organic phase becomes "diluted" with acetic acid and water. Accordingly, the process stabilizes the water balance in the reactor and avoids that critical conditions occur which would necessitate reactor shut-down.

EXAMPLES

The following examples are included to demonstrate preferred embodiments of the invention. It should be appreciated by those skilled in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Infrared spectra of all samples were collected on a Nicolet 6700 spectrometer equipped with a single reflection, zinc selenide, attenuated total reflectance (ATR) sample accessory. Component quantification in these samples was carried out via calibration curves generated from several dozen multicomponent standards in which the concentrations of methyl iodide, acetic acid, methyl acetate, water and alkanes were varied independently such that the concentration range of each component exceeded those subsequently observed for actual samples. TQ Analyst software, available from Thermo Nicolet, was used to generate and validate partial least squares (PLS) based multivariate calibration plots for each component.

Example 1

Effect of Alkanes on Phase Separation Time

Predetermined amounts of methyl iodide, acetic acid, methyl acetate and water were intimately mixed and were allowed to settle, and the time necessary for phase separation was determined. Subsequently, a predetermined amount of decane was intimately mixed with the mixture of methyl iodide, acetic acid, methyl acetate and water, and the time necessary for phase separation was again determined. The compositions of the investigated mixtures, and the results of the investigations, are compiled in the following Table 1.

TABLE 1

The amounts of methyl iodide, acetic acid, methyl acetate, water, and decane are indicated in wt. %.

| | $H_3C-I$ | $H_3CCO_2H$ | $H_3CCO_2CH_3$ | $H_2O$ | $C_{10}H_{12}$ | No. of Phases | Time [sec] |
|---|---|---|---|---|---|---|---|
| 1.01.a | 56.7 | 27.88 | 8.23 | 7.19 | 0 | 1 | ∞ |
| 1.01.b | 56.36 | 27.71 | 8.18 | 7.15 | 0.6 | 2 | 18 |
| 1.02.a | 60.35 | 23.95 | 8.45 | 7.25 | 0 | 2 | 27 |
| 1.02.b | 59.51 | 23.61 | 8.33 | 7.15 | 1.4 | 2 | 14 |

As seen in rows 1 and 2 of Table 1, a low water, alkane free composition (1.01.a) after preparation, remained as a cloudy single phase. Addition of only 0.6 wt. % of decane (1.01.b) led to phase separation within 18 seconds. Experiments (1.02.a) and (1.02.b) illustrate that the addition of 1.4 wt. % of decane reduced the phase separation time by about half, from 27 seconds without the alkane to 14 seconds after addition of the alkane.

Example 2

Effect of Alkanes on Heavy Phase Composition

Predetermined amounts of methyl iodide, acetic acid, methyl acetate and water were intimately mixed and were allowed to settle, and the volume of the heavy phase was determined. Subsequently, a predetermined amount of decane was intimately mixed with the mixture of methyl iodide, acetic acid, methyl acetate and water, and the volume of the heavy phase (HP) was again determined. The compositions of the investigated mixtures, and the results of the investigations, are compiled in Table 2.

TABLE 2

The amounts of methyl iodide, acetic acid, methyl acetate, water, and decane are indicated in wt. %.

| | $H_3C-I$ | $H_3CCO_2H$ | $H_3CCO_2CH_3$ | $H_2O$ | $C_{10}H_{12}$ | No. of Phases | % Vol. HP |
|---|---|---|---|---|---|---|---|
| 2.01.a | 47.47 | 32.03 | 10.08 | 10.42 | 0 | 2 | 46.4 |
| 2.01.b | 46.42 | 31.33 | 9.86 | 10.19 | 2.2 | 2 | 96.4 |

Although the solution (2.01.a) separated into two phases, the volume of the heavy phase was less than 50% of what was expected based on the methyl iodide content of the mixture, indicating that methyl iodide was present in both of the two phases. The addition of 2.2 wt. % of decane (2.01.b) followed by shaking led to phase separation and the heavy phase volume increased to 96% of the expected volume based on the cumulative volume of the alkane and methyl iodide. The result indicates that methyl iodide (along with the alkane) was present almost exclusively in the heavy phase.

Example 3

Effect of Alkanes on Heavy Phase Composition, Heavy Phase Density and Phase Separation Time A starting mixture consisting of 45.6 wt. % methyl iodide, 31.2 wt. % acetic acid, 11.6 wt. % methyl acetate, and 11.6 wt. % water was prepared at room temperature and phase separation time was determined after shaking. The heavy phase was sampled by syringe and analyzed by FTIR. Subsequently, 13 aliquots of a 50/50 decane/3-methylpentane mixture were added successively. After each addition, the solution was shaken and phase separation time was determined.

The heavy phase was also sampled after each addition for FTIR analysis. Phase separation time (PST), heavy phase component concentrations, and heavy phase densities are compiled in Table 3.

TABLE 3

Heavy Phase Data; Amounts are indicated in wt. %, density is indicated in $g/cm^3$, and phase separation time (PST) is indicated in seconds.

| | $H_3C-I$ | $H_3CCO_2H$ | $H_3CCO_2CH_3$ | $H_2O$ | Alkanes | Balance | Density | PST |
|---|---|---|---|---|---|---|---|---|
| 3.00 | 67.21 | 17.14 | 11.61 | 3.88 | 0.00 | 99.84 | 1.611 | 60 |
| 3.01 | 68.04 | 16.38 | 12.25 | 3.41 | 0.50 | 100.58 | 1.601 | 28 |
| 3.02 | 68.82 | 15.03 | 12.14 | 3.01 | 1.12 | 100.12 | 1.602 | 21 |
| 3.03 | 69.57 | 13.86 | 12.22 | 2.55 | 2.29 | 100.49 | 1.599 | 17.5 |
| 3.04 | 70.21 | 12.61 | 12.15 | 2.24 | 2.96 | 100.17 | 1.603 | 14.5 |
| 3.05 | 70.37 | 11.41 | 11.94 | 1.96 | 4.15 | 99.83 | 1.597 | 13 |
| 3.06 | 69.83 | 10.38 | 12.02 | 1.59 | 5.84 | 99.66 | 1.567 | 14 |
| 3.07 | 69.68 | 9.43 | 11.85 | 1.33 | 7.48 | 99.77 | 1.544 | 14 |
| 3.08 | 69.80 | 8.15 | 11.42 | 1.03 | 9.39 | 99.79 | 1.526 | 15 |
| 3.09 | 68.97 | 7.52 | 11.18 | 0.85 | 11.36 | 99.88 | 1.497 | 16.5 |
| 3.10 | 69.00 | 6.65 | 10.58 | 0.65 | 13.26 | 100.14 | 1.48 | 22 |
| 3.11 | 67.60 | 6.00 | 10.28 | 0.5. | 15.83 | 100.19 | 1.438 | 36 |
| 3.12 | 66.84 | 5.53 | 9.95 | 0.36 | 17.72 | 100.40 | 1.412 | 43.5 |
| 3.13 | 65.07 | 4.81 | 9.43 | 0.22 | 20.88 | 100.41 | 1.366 | 70 |

As seen from the data in Table 3, the sequential addition of the alkanes gave rise to a number of different effects. On the one hand, the cumulative addition of alkanes resulted in a dilution of vial components by about 20%. As the alkanes migrate exclusively to the organic phase, it would have been expected that if alkanes have no effect on component distribution between phases, i.e., all heavy phase components should have been diluted equally by 20%. Clearly this is not the case as evidenced by the data. Rather, water and acetic acid, the two components least miscible with alkanes were preferentially ejected from the heavy phase when the alkanes were added. In fact, for the first six aliquots of alkanes added, the loss of acetic acid and water from the heavy phase was so great that the methyl iodide concentration in the heavy phase actually increased slightly in spite of the dilution of the heavy phase by the alkanes. In terms of density, the increase in the methyl iodide concentration was sufficient to offset the effects of the increasing alkanes concentration and the density of the heavy phase was essentially invariant at about 1.60 g/cm$^3$.

Despite this invariance in heavy phase density over the first six additions of alkanes, the phase separation time decreased from 60 seconds to 13 seconds. As the two variables that largely determine phase separation time, namely heavy phase density and heavy phase polarity, have been separated, it is clear that the increasing heavy phase polarity significantly decreases the separation time. A decreased heavy phase polarity results due to the decreased water and acetic acid concentration which accompany the increased amount of alkanes in the heavy phase.

Figure 3:
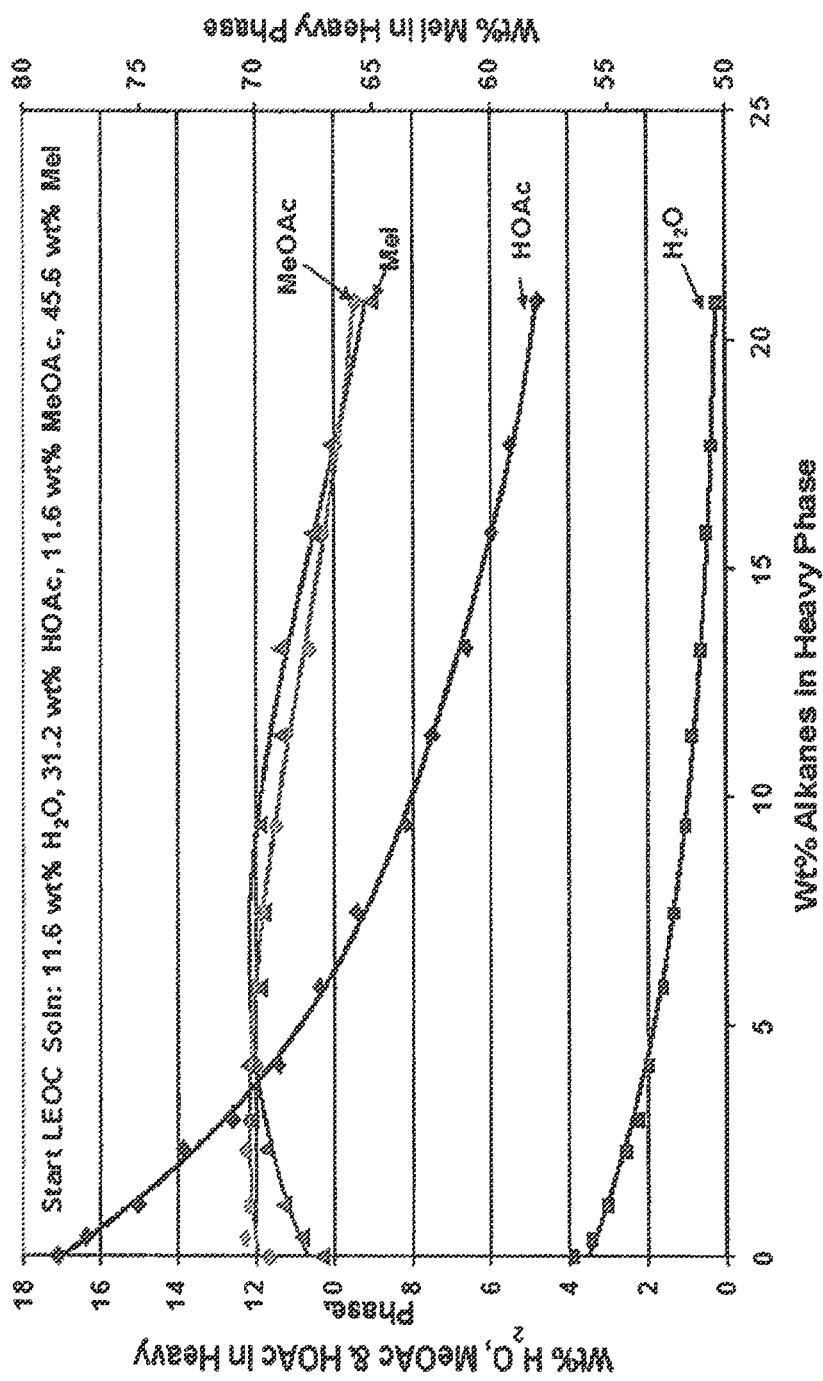
FIG. 3 illustrates the effect of alkanes on the composition of the heavy phase of a mixture of methyl iodide acetic acid, methyl acetate, water, and varying amounts of alkanes under low water-high acid conditions.
Figure 4:
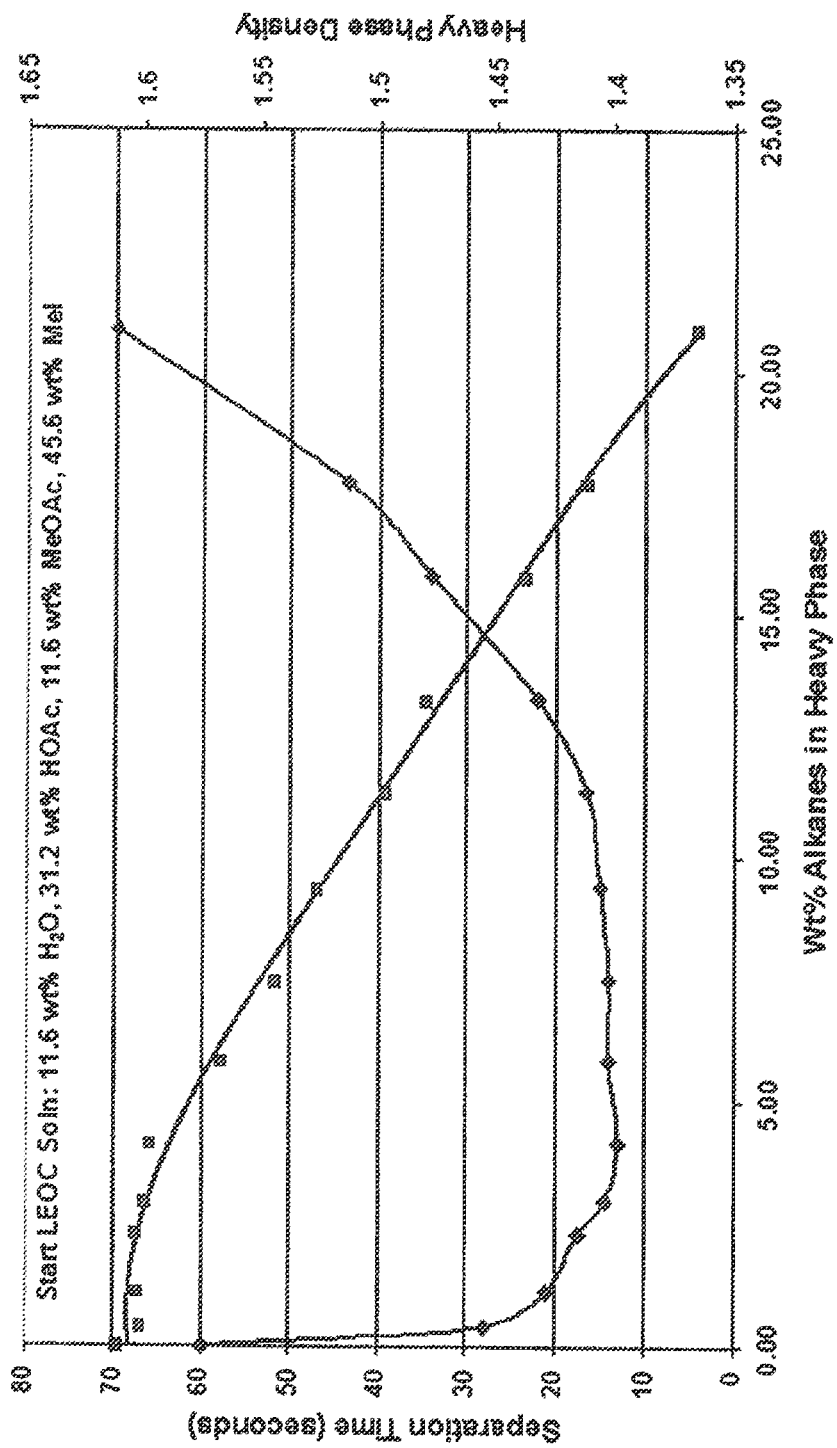
FIG. 4 illustrates the effect of alkanes on the phase separation time, and the density of the heavy phase, of a mixture of methyl iodide acetic acid, methyl acetate, water, and varying amounts of alkanes under low water-high acid conditions.

After addition of several aliquots of alkanes to the point where heavy phase water and acetic acid had been substantially depleted, further alkane addition was accompanied by heavy phase methyl iodide dilution and an accompanying drop in density of the heavy phase. The inverse correlation between alkanes concentration and separation time disappeared and was replaced by a similar inverse correlation between heavy phase density and separation time. The net result was that separation time started to increase again in direct proportion to heavy phase alkanes concentration. Some of these trends are more easily discerned and observed in graphical format. FIG. 3 plots the concentrations of several heavy phase components as a function of alkanes concentration and FIG. 4 illustrates the relationship between alkanes concentration, phase separation time and heavy phase density. The designation "LEOC" in FIGS. 3 and 4 refers to the liquid mixture of methyl iodide, acetic acid, methyl acetate, and water.

Example 4

Comparative

Effect of Alkanes on Heavy Phase Composition, Heavy Phase Density and Phase Separation Time Under High Water-Low Acid Conditions Light phase (LP) compositions A to E as shown in the following Table 4a were prepared in which the water to acetic acid content ranged from about 57:34 to 34:57 wt. %.

TABLE 4a

The amounts of water, acetic acid, methyl acetate, and methyl iodide are indicated in wt. %, the density is indicated in g/cm$^3$.

| | $H_2O$ | $H_3C-CO_2H$ | $H_3C-CO_2CH_3$ | $H_3C-I$ | Density |
|---|---|---|---|---|---|
| 4.LP.A | 57.4 | 33.7 | 4.97 | 3.91 | 1.038 |
| 4.LP.B | 49.64 | 41.19 | 4.85 | 4.32 | 1.042 |
| 4.LP.C | 45.13 | 46.29 | 4.85 | 3.73 | 1.042 |
| 4.LP.D | 40.69 | 50.23 | 4.85 | 4.25 | 1.047 |
| 4.LP.E | 32.79 | 58.91 | 4.67 | 3.63 | 1.047 |

A single heavy phase composition was prepared containing 73.8 wt. % methyl iodide, 11.36 wt. % methyl acetate, 10.98 wt. % alkanes, and 3.97 wt. % acetic acid. 5 ml of each of the light phase compositions A to E were intimately mixed with 5 ml of the heavy phase composition. The mixtures were allowed to settle, and the phase separation time as well as the composition and the density of the resulting heavy phase, was determined.

It was found that the phase separation time, in each case, was about 15 seconds. The data regarding density and composition of the resulting heavy phases (HP) A to E are compiled in Table 4b.

TABLE 4b

The amounts of methyl iodide, alkanes, methyl acetate, acetic acid, and water, are indicated in wt. %, the density is indicated in g/cm$^3$.

| | $H_3C-I$ | Alkanes | $H_3C-CO_2CH_3$ | $H_3C-CO_2H$ | $H_2O$ | Density |
|---|---|---|---|---|---|---|
| 4.HP.A | 77.02 | 11.04 | 8.23 | 3.97 | 0.41 | 1.582 |
| 4.HP.B | 76.56 | 11.36 | 8.27 | 3.42 | 0.34 | 1.584 |
| 4.HP.C | 75.88 | 11.91 | 8.31 | 3.37 | 0.29 | 1.572 |
| 4.HP.D | 75.71 | 12.04 | 8.23 | 4.03 | 0.3 | 1.573 |
| 4.HP.E | 74.64 | 12.63 | 8.21 | 7.79 | 0.29 | 1.579 |

The data show that regardless of the light phase composition, phase separation time was invariant. FTIR analysis of the heavy phase indicates that there was little or no change in chemical composition or density of the heavy phase under high water and low acetic acid conditions.

Example 5

Comparative

Effect of Alkanes on Heavy Phase Composition, Heavy Phase Density and Phase Separation Time Under High Water-Low Acid Conditions Methyl iodide, methyl acetate, acetic acid, and water having an alkanes concentration was varied from 0 to 24 wt. % were intimately mixed, and were allowed to phase separate. Subsequently, the density and composition of the heavy phase was investigated. The results are compiled in Table 5.

TABLE 5

The amounts of methyl iodide, alkanes, methyl acetate, acetic acid, and water, are indicated in wt. %, the density is indicated in g/cm$^3$.

| | $H_3C-I$ | Alkanes | $H_3C-CO_2CH_3$ | $H_3C-CO_2H$ | $H_2O$ | Density |
|---|---|---|---|---|---|---|
| 5.HP.01 | 88.7 | —.— | 8.59 | 3.78 | 0.41 | 1.95 |
| 5.HP.02 | 86.94 | 0.96 | 8.71 | 3.69 | 0.38 | 1.90 |
| 5.HP.03 | 85.76 | 2.39 | 8.55 | 3.63 | 0.37 | 1.89 |
| 5.HP.04 | 84.9 | 3.23 | 8.47 | 3.52 | 0.37 | 1.84 |

TABLE 5-continued

The amounts of methyl iodide, alkanes, methyl acetate, acetic acid, and water, are indicated in wt. %, the density is indicated in g/cm³.

|  | H₃C—I | Alkanes | H₃C—CO₂CH₃ | H₃C—CO₂H | H₂O | Density |
|---|---|---|---|---|---|---|
| 5.HP.05 | 83.4 | 5.03 | 8.26 | 3.44 | 0.35 | 1.79 |
| 5.HP.06 | 80.94 | 7.27 | 8.45 | 3.36 | 0.31 | 1.72 |
| 5.HP.07 | 77.47 | 11.48 | 7.87 | 2.86 | 0.26 | 1.62 |
| 5.HP.08 | 72.96 | 16.72 | 7.42 | 2.60 | 0.21 | 1.51 |
| 5.HP.09 | 67.71 | 22.89 | 6.89 | 2.18 | 0.14 | 1.39 |
| 5.HP.10 | 63.48 | 27.88 | 6.48 | 1.98 | 0.09 | 1.30 |

Heavy phase composition and phase separation time were obtained for each mixture at room temperature. If addition of alkanes to the various mixtures were to have no effect on component distribution between phases, then their only effect would be uniform dilution of all heavy phase components. The data in Table 5 and FIG. 5 allow a comparison of heavy phase compositions and densities as calculated based on the dilution (dashed lines) and based actual values as measured by FTIR (solid lines).

Figure 5:
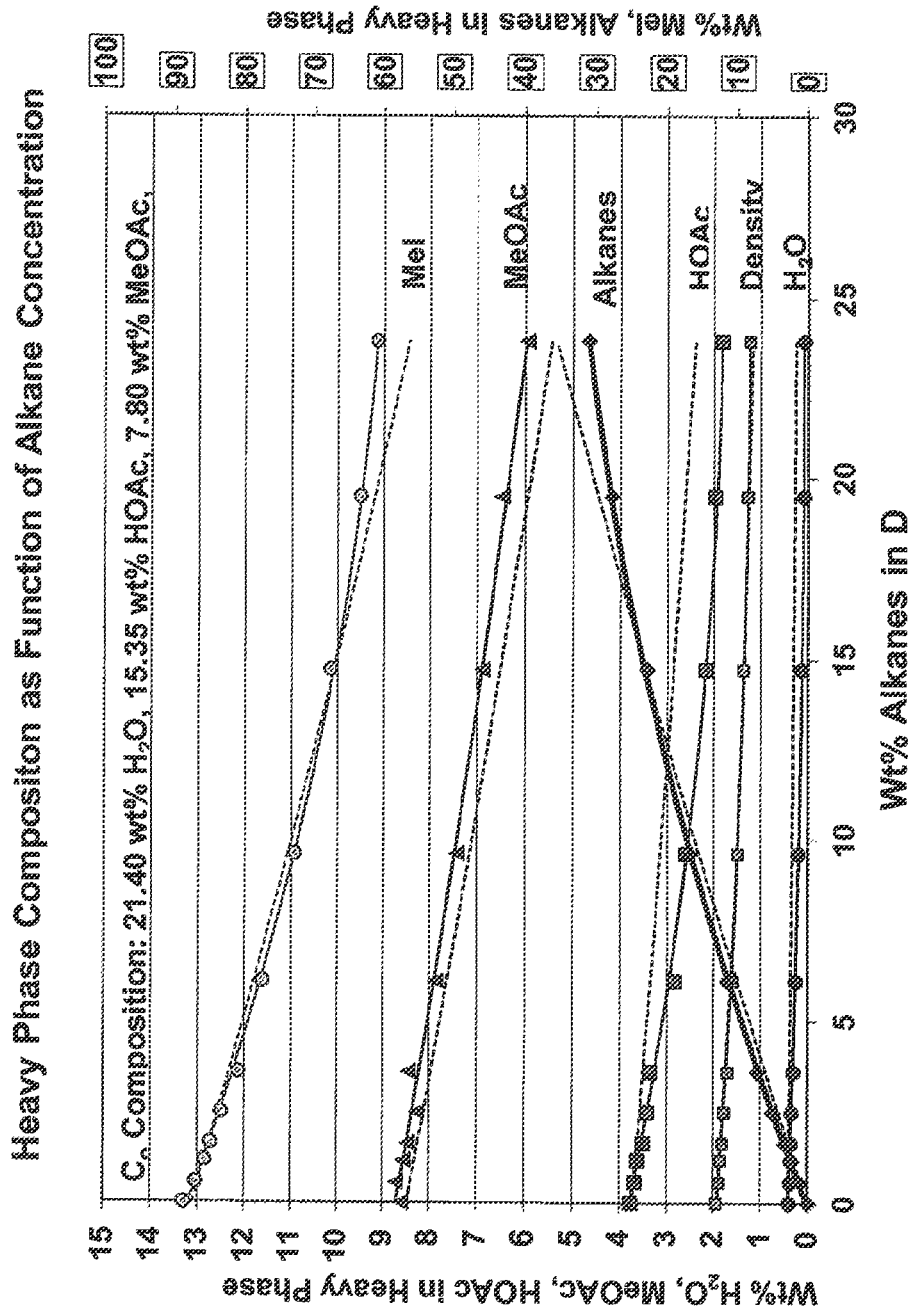
FIG. 5 illustrates the effect of alkanes on the composition of the heavy phase of a mixture of methyl iodide acetic acid, methyl acetate, water, and varying amounts of alkanes under high water-low acid conditions.
Figure 6:
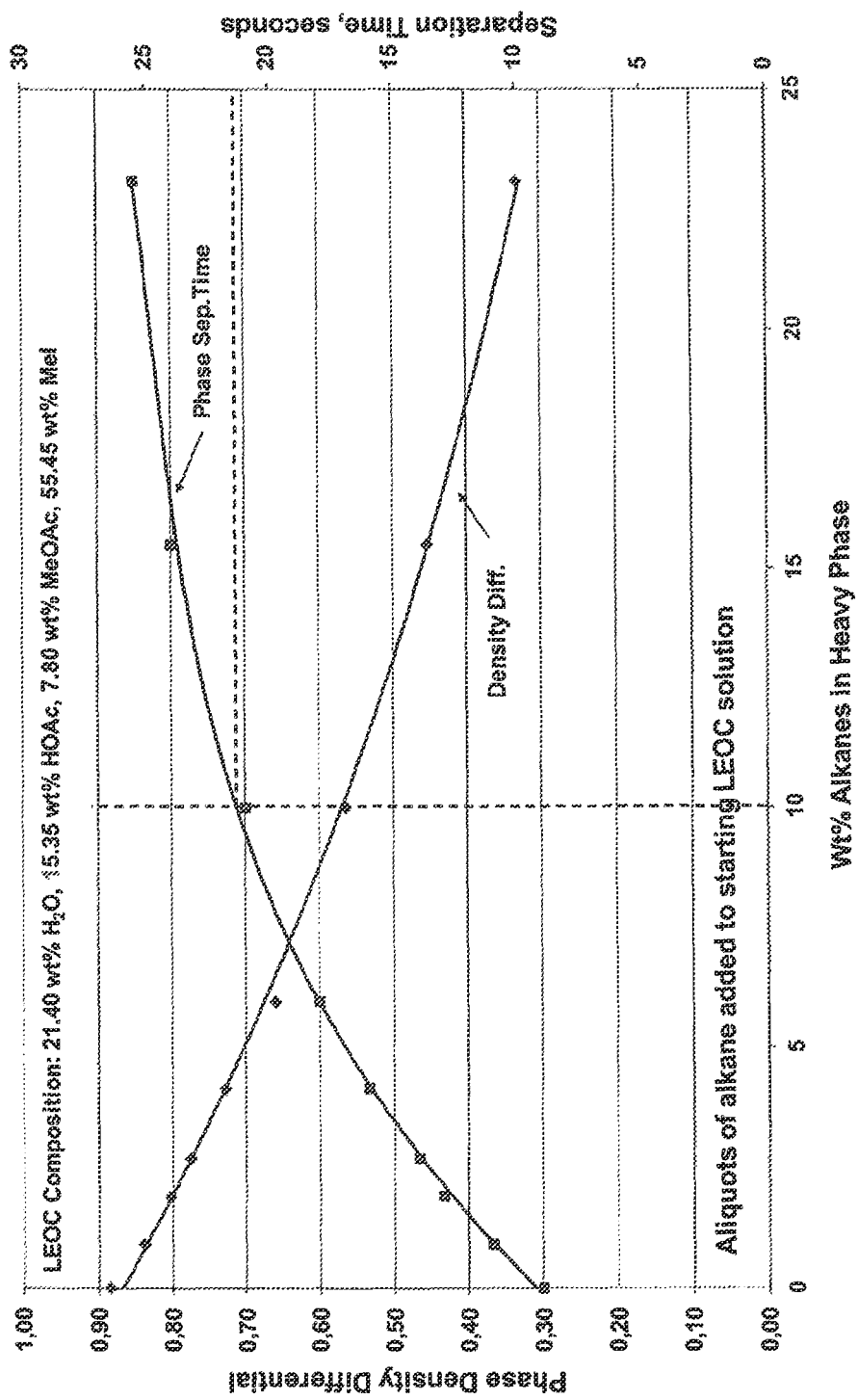
FIG. 6 illustrates the effect of alkanes on the phase separation time, and the density of the heavy phase, of a mixture of methyl iodide acetic acid, methyl acetate, water, and varying amounts of alkanes under high water-low acid conditions.

The data in Table 5 and FIG. 5 show that the measured phase composition and density profiles match very closely to those calculated based on straightforward dilution. Similar to the illustration in FIG. 3, the dilution of water and acetic acid in the heavy phase increases with increasing alkane concentration. However, when large amounts of water and low amounts of acetic acid were present, the dilution effect was comparatively small. As shown in FIG. 6, the phase separation time increased with increasing alkane concentration indicating that the presence of alkanes had no beneficial impact on the phase separation under high water-low acid conditions. The designation "LEOC" in FIG. 6 refers to the liquid mixture of methyl iodide, acetic acid, methyl acetate, and water.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A process for producing acetic acid comprising the steps of:
   (a) carbonylating methanol in the presence of a catalyst in a reaction zone to obtain a reaction mixture comprising acetic acid, methyl acetate, methyl iodide, the catalyst, and water;
   (b) separating at least a part of the reaction mixture in a flash zone to obtain: (i) a liquid stream comprising the catalyst, and (ii) a vapor stream comprising acetic acid, methyl acetate, methyl iodide, and water;
   (c) separating the vapor stream in a fractioning zone to obtain: (i) a product stream comprising acetic acid and water; and, (ii) an overhead stream comprising acetic acid, methyl acetate, methyl iodide, and water;
   (d) condensing the overhead stream and forming a liquid mixture which has a water content of at most 20% by weight, based on the weight of the liquid mixture, a weight ratio of acetic acid to water of at least 1:1, and an alkane content from 0.1 to 15%, based on the weight of the liquid mixture, and
   (e) partitioning the liquid mixture to form an aqueous phase and an organic phase, wherein the aqueous phase comprises acetic acid and water; and the organic phase comprises methyl iodide, methyl acetate and the alkane content
   wherein the step of partitioning the liquid mixture is followed by the step of separating the aqueous phase and the organic phase thereby producing an aqueous stream and an organic stream, and recycling at least a portion of the organic stream to provide the alkanes content of the liquid mixture.

2. The process of claim 1, comprising the steps of:
   separating at least a part of the organic stream to obtain:
   (i) an overhead product comprising methyl iodide and at least a part of the alkanes; and,
   (ii) a bottom product comprising acetic acid, methyl acetate, water and optionally an additional part of the alkanes, and
   recycling the overhead product to the reaction zone,
   maintaining the alkanes content of the overhead stream at from 0.1 to 15% by weight, based on the weight of the condensed overhead stream by adjusting the amount of the organic stream present and by adjusting the separation of the organic stream.

3. The process of claim 2, wherein the step of forming the liquid mixture further comprises the step of adding a component, optionally in combination with innate water, to the condensed overhead stream wherein the component is selected from:
   (i) one or more extraneous or innate alkanes;
   (ii) methyl iodide;
   (iii) acetic acid; or,
   (iv) mixtures thereof, and
   wherein the liquid mixture contains at no more than 20% by weight of water and contains acetic acid and water in a weight ratio of at least 1:1.

4. The process of claim 1, wherein the step of carbonylating methanol further comprises the step of feeding starting materials into the reaction zone wherein the starting materials include: water, methyl acetate, methyl iodide, hydrogen, methanol, carbon dioxide, the catalyst and a catalyst stabilizer; and, wherein the starting material are allowed to react at a temperature ranging from 120° C. to 250° C., and at a pressure of 200 psig to 2000 psig to form the reaction mixture.

5. The process of claim 4, wherein the reaction mixture comprises:
   (i) from 35 to 90% by weight of methyl iodide,
   (ii) from 5 to 35% by weight of acetic acid,
   (iii) from 5 to 15% by weight of water, and
   (iv) up to 15% by weight of methyl acetate,
   wherein the weight percentages are based on the total weight of the components (i) to (iv), and wherein the weight ratio of acetic acid to water in the mixture is at least 1:1.

6. The process of claim 3, wherein the extraneous or innate alkanes have at least 5 carbon atoms.

7. The process of claim 1, wherein the overhead stream comprises at most 17% by weight of water.

8. The process of claim 1, wherein the weight ratio of acetic acid to water in the overhead stream is at least 1.5:1.

9. The process of claim 1, wherein the overhead stream comprises at least 15% by weight acetic acid.

10. The process of claim 1, wherein the overhead stream comprises at least 30% by weight methyl iodide.

11. The process of claim 1, wherein the alkanes content in the liquid mixture is at least 0.5% by weight.

12. The process of claim 1, wherein the alkanes content in the liquid mixture is at most 13% by weight.

13. The process of claim 1, wherein the catalyst is a rhodium catalyst or an iridium catalyst.

14. The process of claim 1, wherein the step of carbonylating methanol takes place in the presence of the catalyst, a catalyst stabilizer and a co-catalyst.

15. The process of claim 14, wherein the catalyst is a rhodium catalyst or an iridium catalyst.

16. The process of claim 15, wherein the catalyst stabilizer is a metal iodide salt or non-salt stabilizer.

17. The process of claim 16, wherein the co-catalyst is a metal or metal compound selected from the group consisting of osmium, rhenium, ruthenium, cadmium, mercury, zinc, gallium, indium, tungsten and mixtures thereof.

18. The process of claim 5, wherein the catalyst is present in a concentration of from about 1.0 mmol to about 100 mmol of catalyst per liter of the reaction mixture.

* * * * *